(12) United States Patent
Panescu et al.

(10) Patent No.: US 10,368,054 B2
(45) Date of Patent: Jul. 30, 2019

(54) QUANTITATIVE THREE-DIMENSIONAL IMAGING OF SURGICAL SCENES

(71) Applicant: Intuitive Surgical Operations, Inc., Sunnyvale, CA (US)

(72) Inventors: Dorin Panescu, San Jose, CA (US); Daniel H Jones, Alexandria, VA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 72 days.

(21) Appl. No.: 15/300,255

(22) PCT Filed: Mar. 28, 2015

(86) PCT No.: PCT/US2015/023210
§ 371 (c)(1),
(2) Date: Sep. 28, 2016

(87) PCT Pub. No.: WO2015/149040
PCT Pub. Date: Oct. 1, 2015

(65) Prior Publication Data
US 2017/0188011 A1    Jun. 29, 2017

Related U.S. Application Data

(60) Provisional application No. 61/971,749, filed on Mar. 28, 2014.

(51) Int. Cl.
*H04N 13/25* (2018.01)
*A61B 1/00* (2006.01)
(Continued)

(52) U.S. Cl.
CPC ......... *H04N 13/25* (2018.05); *A61B 1/00009* (2013.01); *A61B 1/04* (2013.01);
(Continued)

(58) Field of Classification Search
None
See application file for complete search history.

(56) References Cited

U.S. PATENT DOCUMENTS 5,704,897 A    1/1998   Truppe
5,749,362 A    5/1998   Funda et al.
(Continued)

FOREIGN PATENT DOCUMENTS

CA    2859998 A1    5/2013
CN    1874734 A    12/2006
(Continued)

OTHER PUBLICATIONS

Eltaib, M.E.H., et al., "Tactile Sensing Technology for Minimal Access Surgery—a Review," Mechatronics, Pergamon Press, Oxford, GB, vol. 13(10), Dec. 1, 2003 (Dec. 1, 2003), pp. 1163-1177, XP004448741, DOI: 10.1016/S0957-4158(03)00048-5.
(Continued)

*Primary Examiner* — Eileen M Adams
(74) *Attorney, Agent, or Firm* — Schwegman Lundberg & Woessner, P.A.

(57) ABSTRACT

A device is provided that includes an endoscope; an image sensor array is disposed to image a field of view adjacent to the endoscope, each sensor includes a pixel array that is separate from the pixel arrays of other sensors; and a light source is disposed to illuminate the field of view.

10 Claims, 24 Drawing Sheets

(51) Int. Cl.
  *A61B 1/05*      (2006.01)
  *A61B 34/30*     (2016.01)
  *G06T 7/73*      (2017.01)
  *H04N 13/254*    (2018.01)
  *H04N 13/302*    (2018.01)
  *H04N 13/275*    (2018.01)
  *A61B 1/04*      (2006.01)
  *A61B 1/06*      (2006.01)
  *G06T 7/00*      (2017.01)
  *G06T 19/20*     (2011.01)
  *A61B 34/37*     (2016.01)
  *H04N 13/207*    (2018.01)

(52) U.S. Cl.
  CPC .............. *A61B 1/051* (2013.01); *A61B 1/06* (2013.01); *A61B 34/30* (2016.02); *G06T 7/0014* (2013.01); *G06T 7/74* (2017.01); *G06T 19/20* (2013.01); *H04N 13/254* (2018.05); *H04N 13/275* (2018.05); *H04N 13/302* (2018.05); *A61B 34/37* (2016.02); *G06T 2200/04* (2013.01); *G06T 2200/24* (2013.01); *G06T 2207/10068* (2013.01); *G06T 2219/2016* (2013.01); *H04N 13/207* (2018.05); *H04N 2213/001* (2013.01)

(56) References Cited

U.S. PATENT DOCUMENTS

| | | |
|---|---|---|
| 5,833,633 A | 11/1998 | Sarvazyan et al. |
| 6,346,940 B1 | 2/2002 | Fukunaga |
| 6,491,702 B2 | 12/2002 | Heilbrun et al. |
| 6,503,195 B1 | 1/2003 | Keller et al. |
| 6,522,906 B1 | 2/2003 | Salisbury, Jr. et al. |
| 6,650,927 B1 | 11/2003 | Keidar |
| 6,932,610 B2 | 8/2005 | Ono et al. |
| 6,950,550 B1 | 9/2005 | Sumi et al. |
| 7,728,868 B2 | 6/2010 | Razzaque et al. |
| 7,907,166 B2 | 3/2011 | Lamprecht et al. |
| 8,231,522 B2 | 7/2012 | Endo et al. |
| 8,262,559 B2 | 9/2012 | Krattiger |
| 8,334,900 B2 | 12/2012 | Qu et al. |
| 8,514,491 B2 | 8/2013 | Duparre |
| 8,861,089 B2 | 10/2014 | Duparre |
| 8,866,920 B2 | 10/2014 | Venkataraman et al. |
| 8,902,321 B2 | 12/2014 | Venkataraman et al. |
| 9,041,829 B2 | 5/2015 | Venkataraman et al. |
| 9,060,142 B2 | 6/2015 | Venkataraman et al. |
| 9,119,552 B2 | 9/2015 | Baumann et al. |
| 9,188,765 B2 | 11/2015 | Venkataraman et al. |
| 9,235,898 B2 | 1/2016 | Venkataraman et al. |
| 9,264,610 B2 | 2/2016 | Duparre |
| 9,485,496 B2 | 11/2016 | Venkataraman et al. |
| 1,005,215 A1 | 8/2018 | Frimer et al. |
| 2001/0051761 A1 | 12/2001 | Khadem |
| 2002/0022765 A1 | 2/2002 | Belson |
| 2002/0049375 A1 | 4/2002 | Strommer et al. |
| 2003/0036714 A1 | 2/2003 | Kuth et al. |
| 2003/0158477 A1 | 8/2003 | Panescu |
| 2003/0181800 A1 | 9/2003 | Bonutti |
| 2003/0220541 A1 | 11/2003 | Salisbury et al. |
| 2005/0151839 A1 | 7/2005 | Ito et al. |
| 2005/0182295 A1 | 8/2005 | Soper et al. |
| 2005/0219205 A1 | 10/2005 | Bailey et al. |
| 2005/0254720 A1 | 11/2005 | Tan et al. |
| 2006/0183992 A1 | 8/2006 | Kawashima et al. |
| 2006/0281971 A1 | 12/2006 | Sauer et al. |
| 2007/0055128 A1 | 3/2007 | Glossop et al. |
| 2007/0060792 A1 | 3/2007 | Draxinger et al. |
| 2007/0083098 A1 | 4/2007 | Stern et al. |
| 2007/0135803 A1 | 6/2007 | Belson |
| 2007/0147707 A1 | 6/2007 | Coste-Maniere et al. |
| 2007/0151391 A1 | 7/2007 | Larkin et al. |
| 2007/0171369 A1 | 7/2007 | Grundig |
| 2007/0236514 A1 | 10/2007 | Agusanto et al. |
| 2007/0276501 A1 | 11/2007 | Betz et al. |
| 2008/0004603 A1 | 1/2008 | Larkin et al. |
| 2008/0009674 A1* | 1/2008 | Yaron ................ G06T 19/003 600/117 |
| 2008/0058593 A1 | 3/2008 | Gu |
| 2008/0071140 A1 | 3/2008 | Gattani et al. |
| 2008/0188716 A1 | 8/2008 | Heckele et al. |
| 2008/0207997 A1 | 8/2008 | Higgins et al. |
| 2009/0043161 A1 | 2/2009 | Doi |
| 2009/0054910 A1 | 2/2009 | Zheng et al. |
| 2009/0076476 A1 | 3/2009 | Barbagli et al. |
| 2009/0088634 A1 | 4/2009 | Zhao et al. |
| 2009/0088897 A1 | 4/2009 | Zhao et al. |
| 2009/0133260 A1 | 5/2009 | Durbin et al. |
| 2009/0157059 A1 | 6/2009 | Allen et al. |
| 2009/0189749 A1 | 7/2009 | Salada et al. |
| 2009/0192524 A1 | 7/2009 | Itkowitz et al. |
| 2009/0221908 A1 | 9/2009 | Glossop et al. |
| 2009/0259102 A1* | 10/2009 | Koninckx .......... A61B 1/00181 600/111 |
| 2009/0306474 A1* | 12/2009 | Wilson ................ A61B 1/041 600/109 |
| 2009/0317727 A1* | 12/2009 | Beck .................... B82Y 10/00 430/5 |
| 2010/0111389 A1 | 5/2010 | Strobel et al. |
| 2010/0149183 A1 | 6/2010 | Loewke et al. |
| 2010/0169815 A1 | 7/2010 | Zhao et al. |
| 2010/0249506 A1 | 9/2010 | Prisco et al. |
| 2010/0281370 A1 | 11/2010 | Rohaly et al. |
| 2010/0312096 A1 | 12/2010 | Guttman et al. |
| 2010/0312129 A1 | 12/2010 | Schecter et al. |
| 2011/0032088 A1 | 2/2011 | Kim et al. |
| 2011/0044521 A1 | 2/2011 | Tewfik et al. |
| 2011/0122229 A1 | 5/2011 | Cinquin et al. |
| 2011/0163946 A1 | 7/2011 | Tartz et al. |
| 2011/0193938 A1 | 8/2011 | Oderwald et al. |
| 2011/0282143 A1 | 11/2011 | Matsumoto |
| 2011/0282151 A1 | 11/2011 | Trovato et al. |
| 2012/0041345 A1 | 2/2012 | Rajamani et al. |
| 2012/0063644 A1 | 3/2012 | Popovic et al. |
| 2012/0101370 A1 | 4/2012 | Razzaque et al. |
| 2012/0139828 A1 | 6/2012 | Lok et al. |
| 2012/0155731 A1 | 6/2012 | Weersink et al. |
| 2012/0182294 A1 | 7/2012 | Cordon et al. |
| 2012/0265062 A1 | 10/2012 | Sliwa et al. |
| 2012/0289777 A1 | 11/2012 | Chopra et al. |
| 2013/0035583 A1 | 2/2013 | Park et al. |
| 2013/0038689 A1 | 2/2013 | McDowall |
| 2013/0079620 A1 | 3/2013 | Kuth et al. |
| 2013/0197357 A1 | 8/2013 | Green et al. |
| 2013/0202676 A1 | 8/2013 | Koob et al. |
| 2013/0211244 A1 | 8/2013 | Nathaniel et al. |
| 2013/0230837 A1 | 9/2013 | Meglan et al. |
| 2013/0250081 A1 | 9/2013 | Pandey |
| 2013/0296872 A1 | 11/2013 | Davison et al. |
| 2013/0321262 A1 | 12/2013 | Schecter et al. |
| 2014/0005684 A1 | 1/2014 | Kim et al. |
| 2014/0039527 A1* | 2/2014 | Avelar ............ A61B 17/06166 606/144 |
| 2014/0071239 A1 | 3/2014 | Yokota et al. |
| 2014/0163359 A1 | 6/2014 | Sholev et al. |
| 2014/0194896 A1 | 7/2014 | Frimer et al. |
| 2014/0253684 A1 | 9/2014 | Kumar et al. |
| 2014/0276093 A1 | 9/2014 | Zeien et al. |
| 2014/0336501 A1 | 11/2014 | Masumoto |
| 2015/0011894 A1 | 1/2015 | Sarrafzadeh et al. |
| 2015/0025316 A1 | 1/2015 | Hasegawa et al. |
| 2015/0031990 A1 | 1/2015 | Boctor et al. |
| 2015/0049167 A1 | 2/2015 | Suzuki et al. |
| 2015/0062299 A1 | 3/2015 | Brown et al. |
| 2015/0112237 A1 | 4/2015 | Amedi et al. |
| 2015/0134095 A1 | 5/2015 | Hemani et al. |
| 2015/0185849 A1 | 7/2015 | Levesque et al. |
| 2015/0209003 A1 | 7/2015 | Halmann et al. |
| 2015/0230869 A1 | 8/2015 | Shim et al. |
| 2015/0271483 A1 | 9/2015 | Sun et al. |
| 2015/0374210 A1 | 12/2015 | Durr et al. |
| 2016/0151646 A1 | 6/2016 | Bonutti et al. |

(56) References Cited

U.S. PATENT DOCUMENTS

| | | | |
|---|---|---|---|
| 2017/0172662 | A1 | 6/2017 | Panescu et al. |
| 2017/0180704 | A1 | 6/2017 | Panescu et al. |
| 2017/0181798 | A1 | 6/2017 | Panescu et al. |
| 2017/0181808 | A1 | 6/2017 | Panescu et al. |
| 2017/0181809 | A1 | 6/2017 | Panescu et al. |
| 2017/0212723 | A1 | 7/2017 | Atarot et al. |

FOREIGN PATENT DOCUMENTS

| | | | |
|---|---|---|---|
| CN | 101065052 A | 10/2007 | |
| CN | 102046065 A | 5/2011 | |
| CN | 102625670 A | 8/2012 | |
| CN | 102711650 A | 10/2012 | |
| CN | 102781303 A | 11/2012 | |
| CN | 102908158 A | 2/2013 | |
| CN | 103108602 A | 5/2013 | |
| CN | 103269430 A | 8/2013 | |
| CN | 103315696 A | 9/2013 | |
| CN | 103596521 A | 2/2014 | |
| EP | 1826726 A1 | 8/2007 | |
| EP | 2043499 A1 | 4/2009 | |
| EP | 2444006 A2 | 4/2012 | |
| EP | 2548495 A1 | 1/2013 | |
| EP | 2641561 A1 | 9/2013 | |
| JP | H04176429 A | 6/1992 | |
| JP | H04325147 A | 11/1992 | |
| JP | H0630896 A | 2/1994 | |
| JP | H06160087 A | 6/1994 | |
| JP | H07240945 A | 9/1995 | |
| JP | H0998985 A | 4/1997 | |
| JP | H11309 A | 1/1999 | |
| JP | 2000065532 A | 3/2000 | |
| JP | 2002027502 A | 1/2002 | |
| JP | 2002171537 A | 6/2002 | |
| JP | 2003235785 A | 8/2003 | |
| JP | 2005087468 A | 4/2005 | |
| JP | 2005091265 A | 4/2005 | |
| JP | 2006109939 A | 4/2006 | |
| JP | 2006305332 A | 11/2006 | |
| JP | 2009204991 A | 9/2009 | |
| JP | 2010085240 A | 4/2010 | |
| JP | 2011200515 A | 10/2011 | |
| JP | 2012518517 A | 8/2012 | |
| JP | 2013515959 A | 5/2013 | |
| WO | WO-2006080076 A1 | 8/2006 | |
| WO | WO-2007047782 A2 | 4/2007 | |
| WO | WO-2010122145 A1 | 10/2010 | |
| WO | WO-2010147729 A1 | 12/2010 | |
| WO | WO-2012059253 A1 | 5/2012 | |
| WO | WO-2012136223 A1 | 10/2012 | |
| WO | WO-2012155152 A1 | 11/2012 | |
| WO | WO-2013027201 A2 | 2/2013 | |
| WO | WO-2013038403 A2 | 3/2013 | |
| WO | WO-2013134782 A1 | 9/2013 | |
| WO | WO-2014002849 A1 | 1/2014 | |

OTHER PUBLICATIONS

Extended European Search Report for Application No. 15769234.4, dated Oct. 17, 2017, 11 pages.
Garcia O., et al., "Real-time 3D Modeling from Endoscope Image Sequences," ICRA 2009 Workshop—Advanced Sensing and Sensor Integration in Medical Robotics, May 13, 2009 (May 13, 2009). Retrieved from the Internet: URL: http://webdiis.unizar.es/~jcivera/papers/garcia_etal_icra09.pdf [retrieved on Oct. 5, 2017], 3 pages, XP055412801.
Office Action dated Sep. 1, 2017 for Chinese Application No. 201580024436.7 filed Mar. 28, 2015, 25 pages.
Oosten J.V., "Understanding the View Matrix—3D Game Engine Programming 3D Game Engine Programming," Jul. 6, 2011 (Jul. 6, 2017), Retrieved from the Internet: URL: http://www.3dgep.com/understading-the-view-matrix/ [retrieved on Oct. 14, 2015], 34 pages, XP055220667.
Partial Supplementary European Search Report for Application No. 15770100.4, dated Oct. 18, 2017, 17 pages.
Partial Supplementary European Search Report for Application No. EP15770259.8, dated Oct. 24, 2017, 20 pages.
Rigel, D. S., et al., "The Evolution of Melanoma Diagnosis: 25 Years Beyond the ABCDs," CA Cancer J Clin, vol. 60 (5), Jul. 29, 2010 (Jul. 29, 2010), pp. 301-316, XP055384411, ISSN: 0007-9235, DOI: 10.3322/caac.20074.
Thormahlen T., et al., "Three-Dimensional Endoscopy," Falk Symposium, vol. 124, Jan. 1, 2002 (Jan. 1, 2002), 6 pages, XP055413139, ISBN: 978-0-7923-8774-9.
Wu C., "3D Reconstruction of Anatomical Structures from Endoscopic Images," CMU-R1-TR-10-04, Jan. 1, 2010 (Jan. 1, 2010), Retrieved from the Internet: URL:https://www.cs.cmu.edu/-ILIM/publications/PDFs/W-THESIS09.pdf [retrieved on Oct. 5, 2017], pp. 1-113, XP055412730.
Agus M., et al., "Real-time Cataract Surgery Simulation for Training," In Eurographics Italian Chapter Conference, Eurographics Association, 2006, 5 pages.
Coelho M., et al., "Shape-Changing Interfaces," Personal and Ubiquitous Computing, M. Coelho, et al., MIT Media Lab. 75 Amherst St., E14-548H, Cambridge, MA, USA, Springer-Verlag, published online Jul. 29, 2010, vol. 15 (2), pp. 161-173.
Cotin S., et al., "Real-time Elastic Deformations of Soft Tissues for Surgery Simulation," IEEE Transactions on Visualization and Computer Graphics, 1999, vol. 5, pp. 62-73.
Culijat M., et al., "Pneumatic Balloon Actuators for Tactile Feedback in Robotic Surgery," Industrial Robot: An international Journal, 2008, vol. 35 (5), pp. 449-455.
Delingette H., "Simplex Meshes: A General Representation for 3D Shape Reconstruction," Technical Report 2214, INRIA, Mar. 1994, 59 pages.
Follmer S., et al., "inFORM: Dynamic Physical Affordances and Constraints through Shape and Object Actuation," Proceedings of the 26th Annual ACM Symposium on UIST, ACM, 2013,New York, NY, USA, vol. 13, pp. 417-426.
Hassanfiroozi A., et al., Liquid Crystal Lens Array for 3D Endoscope Application, in: Three-Dimensional Imaging, Visualization, and Display, Javidi B., et al., eds., Proceedings of SPIE, vol. 9117 91170E 1-7, 7 pages, [online], [retrieved Aug. 21, 2014]. Retrieved from the Internet: < URL: http://proceedings.spiedigitallibrary.org/>.
Howe, Robert D. et al., "Remote Palpation Technology," IEEE Engineering in Medicine and Biology, 1995, pp. 318-323, vol. 14—Issue 3, IEEE.
International Search Report and Written Opinion for Application No. PCT/US2015/23212, dated Jun. 30, 2015, 8 pages.
International Search Report and Written Opinion for Application No. PCT/US2015/23213; dated Jul. 14, 2015, 13 pages.
International Search Report and Written Opinion for Application No. PCT/US15/23211, dated Jul. 1, 2015, 13 pages.
International Search Report and Written Opinion for Application No. PCT/US15/23217, dated Jun. 29, 2015, 12 pages.
International Search Report and Written Opinion for Application No. PCT/US2015/023214, dated Jun. 29, 2015, 10 pages.
International Search Report and Written Opinion for Application No. PCT/US15/23210, dated Jun. 29, 2015, 17 pages.
Iwata H., et al., "Project FEELEX: Adding Haptic Surface to Graphics," SIGGRAPH'01, 2001, pp. 469-476.
J. Montagnat and H. Delingette, "Volumetric Medical Images Segmentation Using Shape Constrained Deformable Models," Proceedings of CVRMed-MRCAS '97, Grenoble, France,J. Troccaz, E. Grimson, and R. Mosges, eds. Mar. 1997, pp. 13-22.
K. Chinzei and K. Miller, "Compression of Swine Brain Tissue; Experiment in Vitro," Journel of Mechanical Engineering Laboratory, Jul. 1996, vol. 50(4), pp. 106-115.
Killebrew J.H., et al., "A Dense Array Stimulator to Generate Arbitrary Spatia-Temporal Tactile Stimuli," Journal of Neuroscience Methods, 2007. vol. 161 (1), pp. 62-74.
Laks Raghupathi, Laurent Grisoni, Fran?ois Faure, Damien Marchal, Marie-Paule Cani, Christophe Chaillou, "An Intestinal Surgery

(56) References Cited

OTHER PUBLICATIONS

Simulator: Real-Time Collision Processing and Visualization," IEEE Transactions on Visualization and Computer Graphics, vol. 10, No. 6, pp. 708-718, Nov./Dec. 2004.

Monserrat C., et al., "GeRTiSS: A Generic Multi-model Surgery Simulator," Springer-Verlag Berlin Heidelberg, IS4TM 2003. LNCS 2673, 2003, pp. 59-66.

Moore M., et al., "Collision Detection and Response for Computer Animation," Computer Graphics, SIGGRAPH, 1988, vol. 22 (4), pp. 289-298.

Moy G., et al., "A Compliant Tactile Display for Teletaction," Proceedings of ICRA in Robotics and Automation, 2000, IEEE, vol. 4. 7 pages.

Okamura A.M., "Haptic Feedback in Robot-Assisted Minimally Invasive Surgery," Current Opinion in Urology, 2009, vol. 19 (1), pp. 102-107.

Ottermo M.V., et al., "Electromechanical Design of a Miniature Tactile Shape Display for Minimally invasive Surgery," Proceedings of the First Joint Eurohaptics Conference and Symposium on Haptic Interfaces for Virtual Environment and Teleoperator Systems, IEEE, 2005, 2 pages.

Rasmussen M.K., et al., "Shape-Changing Interfaces: A Review of the Design Space and Open Research Questions," Proceedings of the SIGCHI Conference on Human Factors in Computing Systems on CHI, ACM, 2012, pp. 735-744.

Reiley, Carol E. et al., "Effects of visual force feedback on robot-assisted surgical task performance," Journal of Thoracic and Cardiovascular Surgery, Jan. 2008, vol. 35 (1), pp. 196-202.

Vertut, Jean and Phillipe Coiffet, Robot Technology: Teleoperation and Robotics Evolution and Development, English translation: Prentice-Hall, Inc., Inglewood Cliffs, NJ, USA 1986, vol. 3A, 332 pages.

Extended European Search Report for Application No. EP15768409.3, dated Feb. 26, 2018, 9 pages.

Extended European Search Report for Application No. EP15770100.4, dated Feb. 16, 2018, 14 pages.

Extended European Search Report for Application No. EP15770259.8, dated Feb. 2018, 18 pages.

Extended European Search Report for Application No. EP15769289.8, dated Dec. 12, 2017, 11 pages.

Partial Supplementary European Search Report for Application No. 15767964.8, dated Dec. 13, 2017, 17 pages.

Extended European Search Report for Application No. EP15767964.8, dated Apr. 24, 2018, 19 pages.

Office Action dated Jul. 4, 2018 for Chinese Application No. 201580024439.0 filed Mar. 28, 2015, 13 pages.

* cited by examiner

QUANTITATIVE THREE-DIMENSIONAL IMAGING OF SURGICAL SCENES

This application is a U.S. National Stage Filing under 35 U.S.C. 371 from International Application No. PCT/US2015/023210, filed on Mar. 28, 2015, and published as WO 2015/149040 A1 on Oct. 1, 2015, which claims the benefit of priority to U.S. provisional patent application No. 61/971,749, filed on Mar. 28, 2014, and entitled "QUANTITATIVE THREE-DIMENSIONAL IMAGING OF SURGICAL SCENES", each of which is incorporated herein by reference in its entirety.

FIELD

The invention relates in general to surgical endoscopy systems having associated image sensors, and more particularly, to determining three-dimensional coordinates of physical structures displayed in surgical images.

BACKGROUND

Quantitative three-dimensional (Q3D) vision provides numerical information about the actual physical (x, y, z) 3D coordinates of target points in a real world scene. With quantitative 3D vision, a person not only can obtain a three-dimensional perception of a real world scene, but also can obtain numerical information about physical dimensions of objects in the scene and physical distances between objects in the scene. In the past, some Q3D systems have been proposed that use time-of-flight related information or phase information to determine 3D information about a scene. Other Q3D systems have used structured light to determine 3D information about a scene.

The use of time-of-flight information is disclosed in U.S. Pat. No. 6,323,942, entitled, "CMOS-compatible three-dimensional image sensor IC", which discloses a three-dimensional imaging system that includes a two-dimensional array of pixel light sensing detectors fabricated on a common IC using CMOS fabrication techniques. Each detector has an associated high speed counter that accumulates clock pulses in number directly proportional to time-of-flight (TOF) for a system-emitted pulse to reflect from an object point and be detected by a pixel detector focused upon that point. The TOF data provides a direct digital measure of distance from the particular pixel to a point on the object reflecting the emitted light pulse. In a second embodiment, the counters and high speed clock circuits are eliminated, and instead each pixel detector is provided with a charge accumulator and an electronic shutter. The shutters are opened when a light pulse is emitted and closed thereafter such that each pixel detector accumulates charge as a function of return photon energy falling upon the associated pixel detector. The amount of accumulated charge provides a direct measure of round-trip TOF.

The use of time delay information is disclosed in U.S. Pat. No. 8,262,559, entitled, "Apparatus and method for endoscopic 3D data collection", which discloses a modulated measuring beam, a light-transmitting mechanism for conducting the measuring beam onto an area to be observed, where the light-transmitting mechanism includes an illuminating lens, in addition to a light-imaging mechanism for imaging a signal beam from the area to be observed at least onto a phase-sensitive image sensor. Time delays, which may correspond to differences in depth in the mm range, result in phase information that makes possible the production of an image that depicts depth and distance information.

The use of structured light to determine physical coordinates of objects in a visual image is disclosed in U.S. Pat. App. Pub. No. 2012/0190923, entitled "Endoscope"; and in C. Schmalz et al., "An endoscopic 3D scanner based on structured light", Medical Image Analysis, 16 (2012) 1063-1072. A triangulation method is used to measure the topography of a surface. Structured light in the form of projection rays, which may have a range of different color spectra, are incident upon and are reflected from a surface. The reflected rays are observed by a camera that is calibrated to use the reflected color spectra information to determine 3D coordinates of the surface. More specifically, the use of structured light typically involves shining a light pattern on a 3D surface, and determining physical distances based upon a deformation pattern of the light due to contours of the physical object.

An imager array camera has been built that includes a plurality of pixel arrays that can be used to compute scene depth information for pixels in the array. High resolution (HR) images are generated from multiple low resolution (LR) images. A reference viewpoint is selected and an HR image is generated as seen by that viewpoint. A parallax processing technique utilizes the effects of aliasing to determine pixel correspondences for non-reference images with respect to the reference image pixels. Fusion and superresolution are utilized to produce the HR image from the multiple LR images. See, U.S. Pat. No. 8,514,491, entitled "Capturing and Processing Images using Monolithic Camera Array with Heterogeneous Imager"; U.S. Pat. App. Pub. No. 2013/0070060, entitled, Systems and Methods for Determining Depth from multiple Views of a Scene that Include Aliasing using Hypothesized Fusion"; and K. Venkataraman et al., PiCam: An ultra-Thin high Performance Monolithic Camera Array.

FIG. 1 is an illustrative drawing showing details of a known imager sensor 180 in accordance with some embodiments. The image sensor 180 includes an optic array of lens stacks 182 and an array of sensors 184. Each sensor in the array includes a two dimensional arrangement of pixels having at least two pixels in each dimension. Each sensor includes a lens stack 186 that creates a separate optical channel that resolves an image onto a corresponding arrangement of pixels disposed in a focal 188 plane of the lens stack. The pixels act as light sensors and each focal plane 188 with its multiple pixels acts as an image sensor. Each sensor with its focal plane 182 occupies a region of the sensor array different from regions of the sensor array occupied by other sensors and focal planes.

FIG. 2 is an illustrative drawing showing a simplified plan view of the known imager sensor array 180 of FIG. 1 that includes sensors $S_{11}$ through $S_{33}$. The imager sensor array 180 is fabricated on a semiconductor chip to include a plurality of sensors $S_{11}$ through $S_{33}$ Each of the sensors $S_{11}$ through $S_{33}$ includes a plurality of pixels (e.g., 0.32 Mega pixels) and is coupled to peripheral circuitry (not shown) that includes independent read-out control and pixel digitization. In some embodiments, the sensors $S_{11}$ through $S_{33}$ are arranged into a grid format as illustrated in FIG. 2. In other embodiments, the sensors are arranged in a non-grid format. For example, the imagers may be arranged in a circular pattern, zigzagged pattern or scattered pattern or an irregular pattern including sub-pixel offsets.

Each sensor pixel includes a microlens pixel stack. FIG. 3 is an illustrative drawing of a known microlens pixel stack of the sensors of FIGS. 1-2. The pixel stack 800 includes a microlens 802, which sits atop an oxide layer 804, which is typically beneath the oxide layer 804 there may be a color filter 806, which is disposed above a nitride layer 808, which is disposed above a second oxide layer 810, which and sits atop a silicon 812 that layer includes the active area 814 of the sensor (typically a photodiode). The primary role of a microlens 802 is to gather the light incident on its surface and to focus that light onto the small active area 814. The pixel aperture 816 is determined by the spread of the microlens, which collects the light and focuses it on the active area 814.

Additional information concerning the above-described known imager sensor array architecture is provided in U.S. Pat. No. 8,514,491, issued, Aug. 20, 2013; and in U.S. Patent Application Pub. No. 20013/0070060, published Mar. 21, 2013.

SUMMARY

In one aspect, a device includes an endoscope. An image sensor array is disposed to image a field of view adjacent to the endoscope. Each sensor of the sensor array includes a pixel array that is separate from the pixel arrays of other sensors. A light source is disposed to illuminate the field of view.

In another aspect, a method for Q3D imaging is provided in which an image sensor array is provided adjacent a tip of an endoscope. The tip of endoscope is positioned adjacent to a target object. The target object is illuminated with a light source.

In another aspect, a method for Q3D imaging is provided in which a light pipe input is provided adjacent a tip of an endoscope. The tip of endoscope is positioned adjacent to a target object. The target object is illuminated with a light source. The light is used to transmit an image within a field of view of the input to the light pipe to an image sensor array, each sensor in the array including a pixel array that is separate from the pixel arrays of other sensors.

In another aspect, Q3D imaging information is used during surgery to alert a surgeon of proximity between a surgical instrument imaged by the image sensor and a target object imaged by the image sensor.

In another aspect, a visual 3D model of the target object is created using the Q3D imaging information, and the 3D model is manipulated during a surgical procedure.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DESCRIPTION OF EMBODIMENTS

Figure 1:
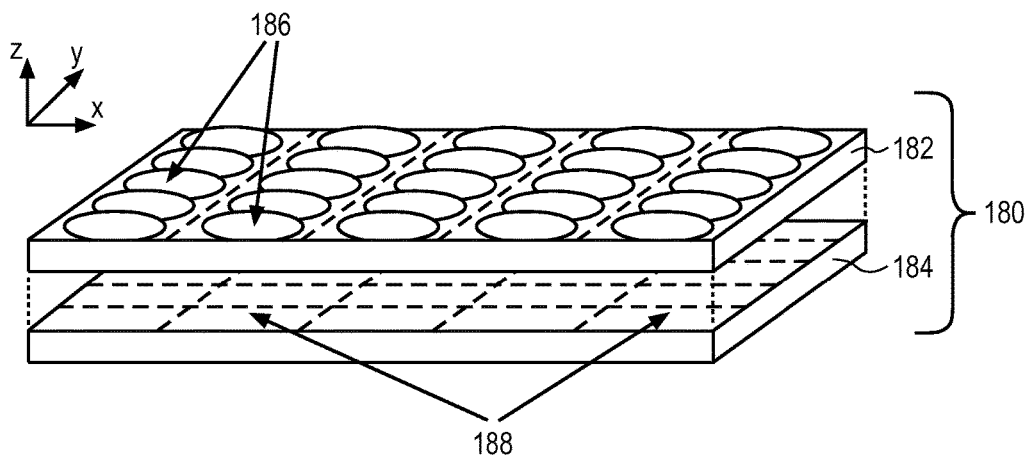
FIG. 1 is an illustrative drawing showing details of a known imager sensor array.
Figure 2:
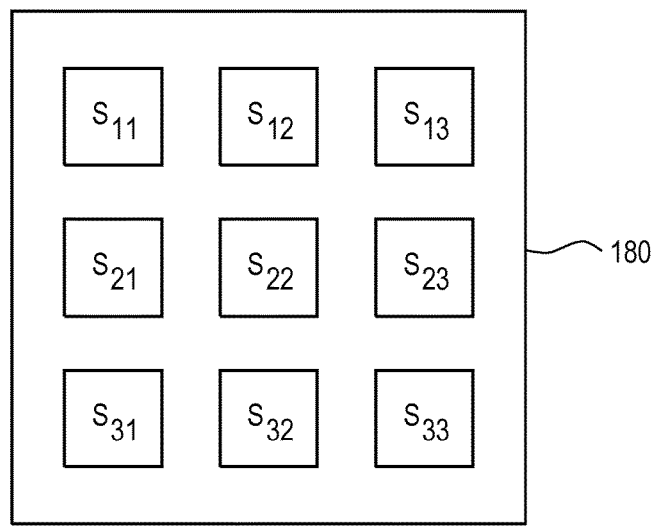
FIG. 2 is an illustrative drawing showing a simplified plan view of a known imager sensor array that includes multiple sensors.
Figure 3:
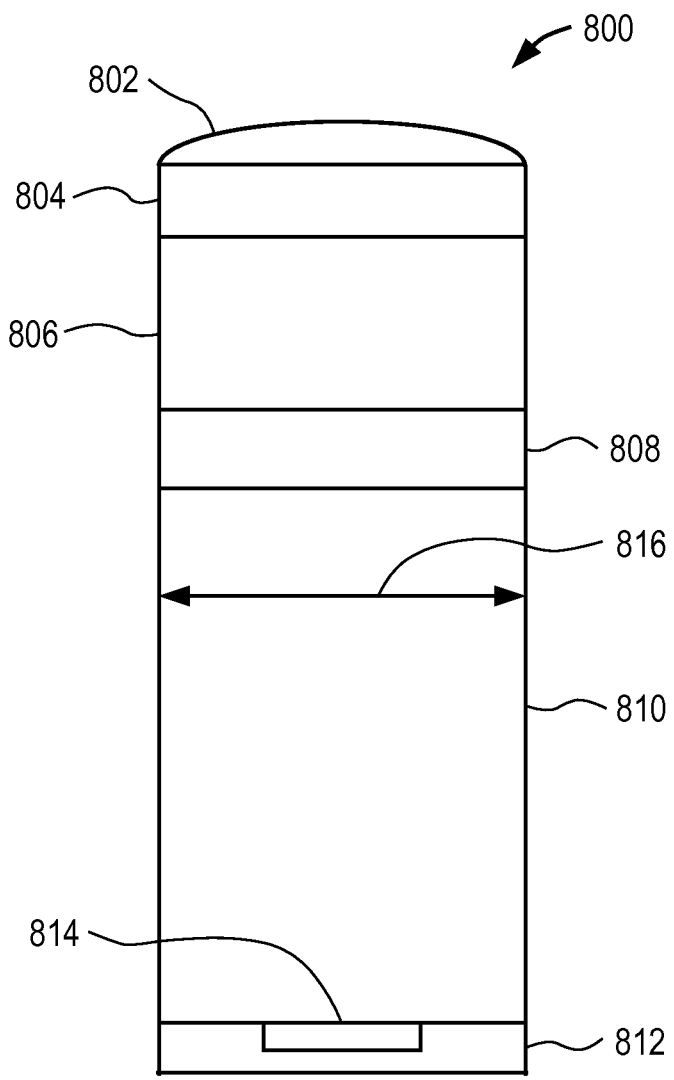
FIG. 3 is an illustrative drawing of a known microlens pixel stack.

The following description is presented to enable any person skilled in the art to create and use a surgical endoscopy system having multiple image sensors, each sensor including a pixel array that is separate from pixel arrays of other sensors, to determine three-dimensional coordinates of physical structures within a field of view of the image sensors. Various modifications to the embodiments will be readily apparent to those skilled in the art, and the generic principles defined herein may be applied to other embodiments and applications without departing from the spirit and scope of the inventive subject matter. Moreover, in the following description, numerous details are set forth for the purpose of explanation. However, one of ordinary skill in the art will realize that the inventive subject matter might be practiced without the use of these specific details. In other instances, well-known machine components, processes and data structures are shown in block diagram form in order not to obscure the disclosure with unnecessary detail. Identical reference numerals may be used to represent different views of the same item in different drawings. Flow diagrams in drawings referenced below are used to represent processes. A computer system may be configured to perform some of these processes. Modules within flow diagrams representing computer implemented processes represent the configuration of a computer system according to computer program code to perform the acts described with reference to these modules. Thus, the inventive subject matter is not intended to be limited to the embodiments shown, but is to be accorded the widest scope consistent with the principles and features disclosed herein.

BRIEF OVERVIEW

In accordance with some embodiments, an image sensor array that includes an imager sensor array is associated with an endoscope. The image sensor array includes multiple sensors and each sensor includes an array of pixels. A portion of the endoscope is inserted into a human body cavity and a target object in a field of view of the image sensor array is illuminated using a light source. A physical location and/or dimensions of the target object is determined based upon projected images of the object onto individual sensors of the array.

Figure 4:
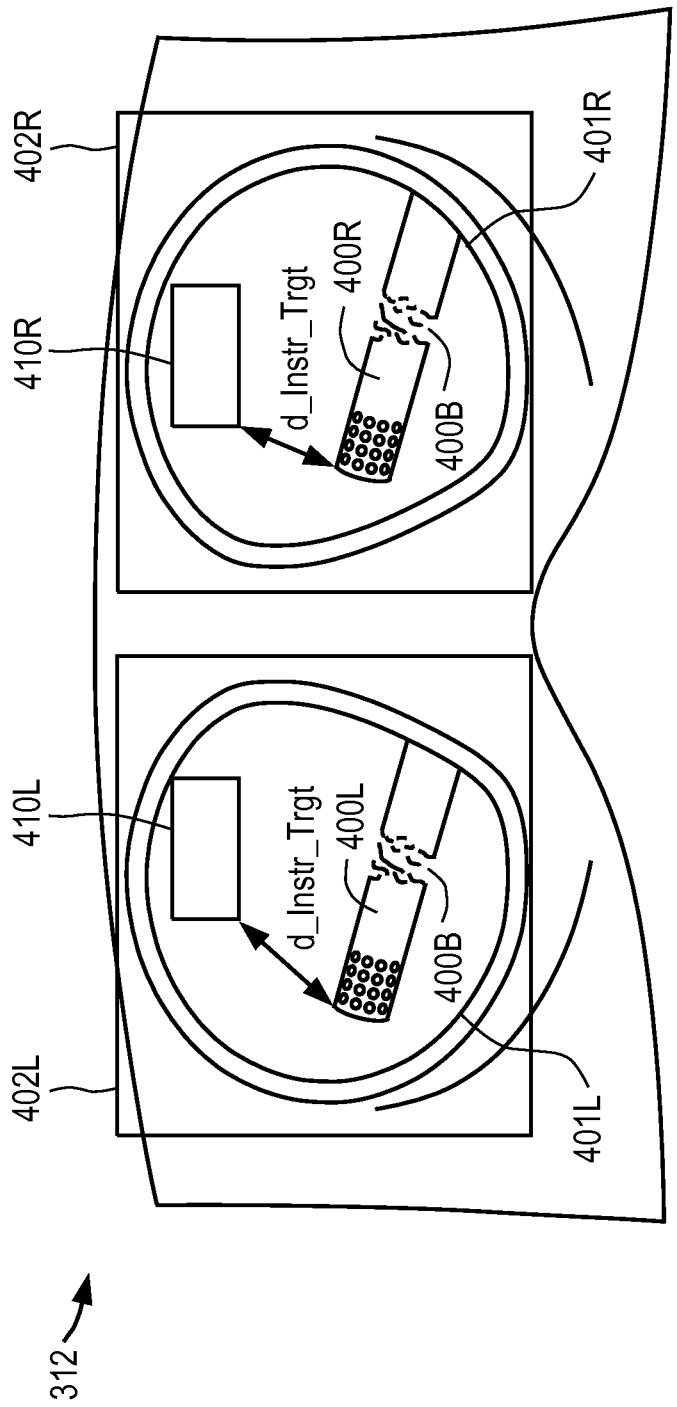
FIG. 4 is an illustrative drawing showing a perspective view of a surgical scene through a viewer in accordance with some embodiments.

FIG. 4 is an illustrative drawing showing a perspective view of a surgical scene through a viewer 312 in accordance with some embodiments. A viewing system having two imaging elements 206R, 206L can provide a good 3D viewing perspective. Numerical values representing physical dimension and/or location information for physical structures in the surgical scene are shown overlaid onto the surgical scene image. For example, a numerical distance value "d_Instr_Trgt" is shown displayed within the scene between instrument 400 and target 410.

Teleoperation Medical System

Teleoperation refers to operation of a machine at a distance. In a minimally invasive teleoperation medical system, a surgeon may use a camera mounted on an endoscope to view a surgical site within a patient's body. Three-dimensional images have been generated to provide high resolution view during surgery. A camera system, which is mounted on an endoscope and which includes an imager sensor array, provides quantitative three-dimensional information plus color and illumination data that can be used to generate three-dimensional images in accordance with some embodiments.

Figure 5:
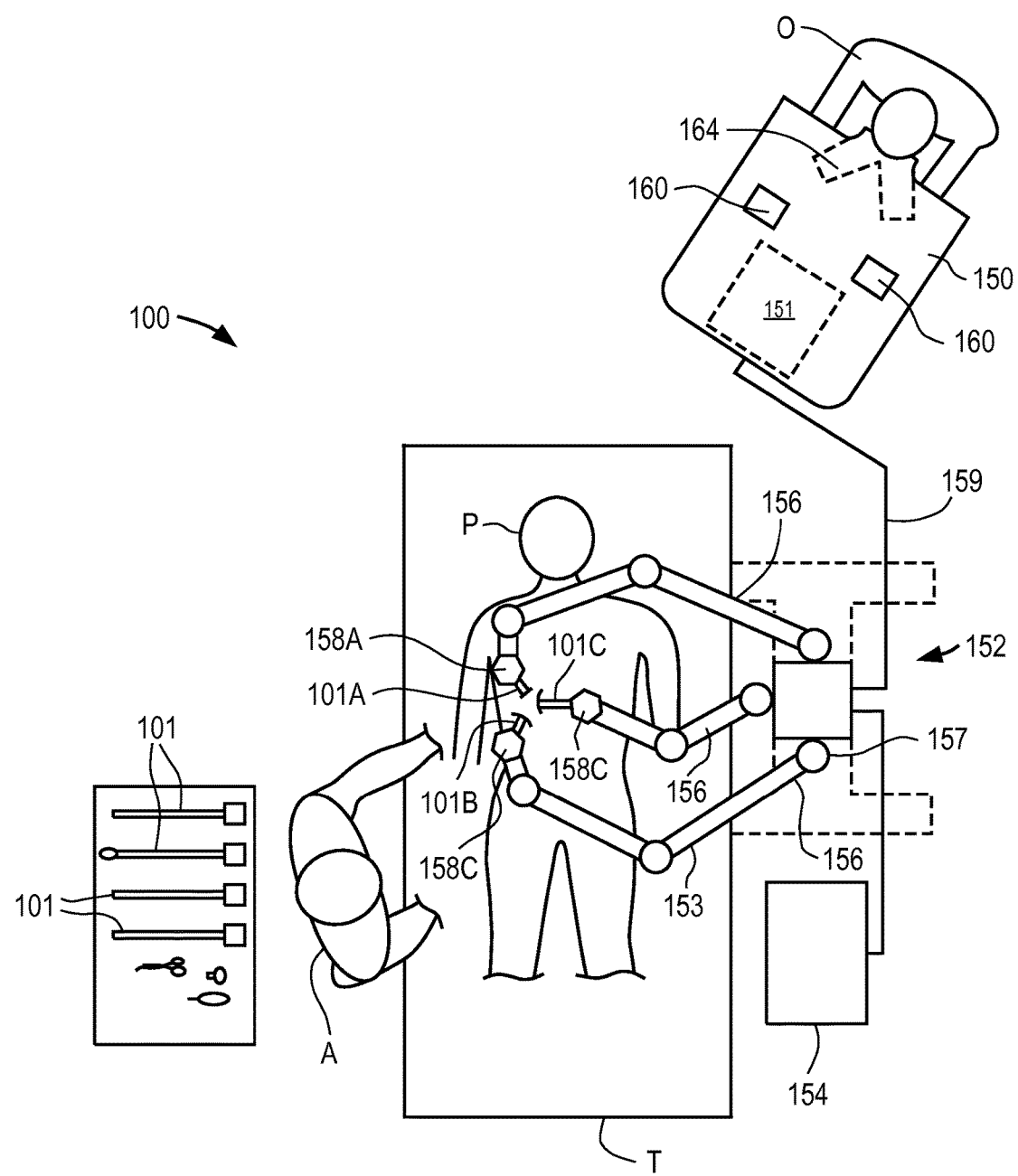
FIG. 5 is an illustrative block diagram of a teleoperation surgery system to perform minimally invasive surgical procedures using one or more mechanical arms in accordance with some embodiments.

FIG. 5 is an illustrative block diagram of a teleoperation surgery system 100 to perform minimally invasive surgical procedures using one or more mechanical arms 158 in accordance with some embodiments. Aspects of system 100 include telerobotic and autonomously operating features. These mechanical arms often support an instrument. For instance, a mechanical surgical arm (e.g., the center mechanical surgical arm 158C) may be used to support a stereo or three-dimensional surgical image capture device 101C such as an endoscope associated a Q3D image sensor array. The mechanical surgical arm 158C may include a sterile adapter, or a clamp, clip, screw, slot/groove or other fastener mechanism to mechanically secure the image capture device 101C to the mechanical arm. Conversely, the image capture device 101C may include physical contours and/or structures complementary to those of the mechanical surgical arm 158C so as to securely interfit with them.

A user or operator O (generally a surgeon) performs a minimally invasive surgical procedure on patient P by manipulating control input devices 160 at a master control console 150. The operator can view video frames of images of a surgical site inside a patient's body through a stereo display device 164, which includes the viewer 312 described above with reference to FIG. 4. A computer 151 of the console 150 directs movement of teleoperationally controlled endoscopic surgical instruments 101A-101C via control lines 159, effecting movement of the instruments using a patient-side system 152 (also referred to as a patient-side cart).

The patient-side system 152 includes one or more mechanical arms 158. Typically, the patient-side system 152 includes at least three mechanical surgical arms 158A-158C (generally referred to as mechanical surgical arms 158) supported by corresponding positioning set-up arms 156. The central mechanical surgical arm 158C may support an endoscopic camera 101C suitable for capture of Q3D information for images within a field of view of the camera. The mechanical surgical arms 158A and 158B to the left and right of center may support instruments 101A and 101B, respectively, which may manipulate tissue.

Figure 6:
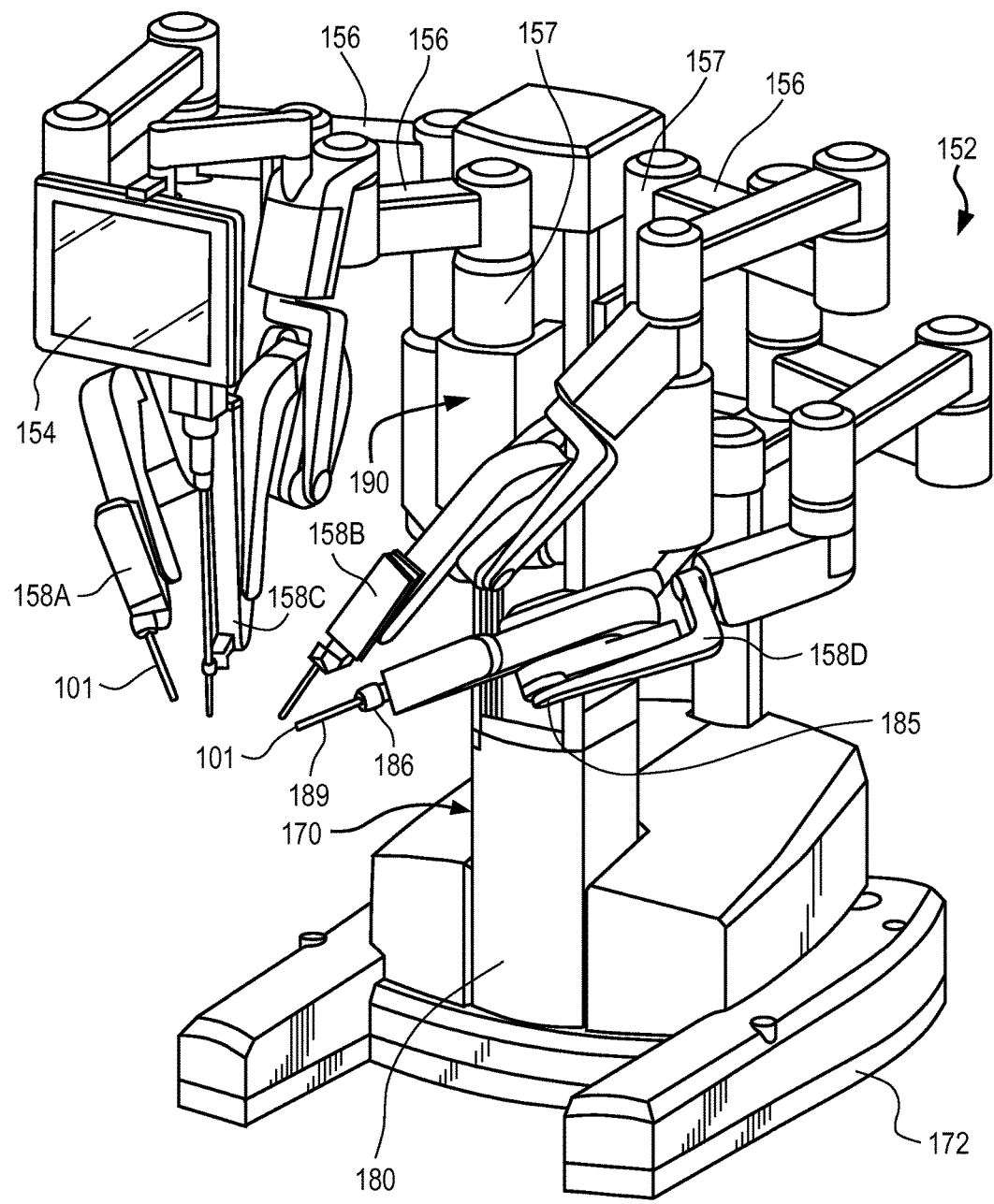
FIG. 6 is an illustrative perspective view of a patient-side system of the system of FIG. 5 in accordance with some embodiments.

FIG. 6 is an illustrative perspective view of the patient-side system 152 in accordance with some embodiments. The patient-side system 152 comprises a cart column 170 supported by a base 172. One or more mechanical surgical arms 158 are respectively attached to one or more set-up arms 156 that are a part of the positioning portion of the patient-side system 152. Situated approximately at a central location on base 172, the cart column 170 includes a protective cover 180 that protects components of a counterbalance subsystem and a braking subsystem from contaminants.

Excluding a monitor arm 154, each mechanical surgical arm 158 is used to control instruments 101A-101C. Moreover, each mechanical surgical arm 158 is coupled to a set-up arm 156 that is in turn coupled to a carriage housing 190 in one embodiment of the invention. The one or more mechanical surgical arms 158 are each supported by their respective set-up arm 156, as is illustrated in FIG. 6.

The mechanical surgical arms 158A-158D may each include one or more displacement transducers, orientational sensors, and/or positional sensors 185 to generate raw uncorrected kinematics data, kinematics datum, and/or kinematics information to assist in acquisition and tracking of instruments. The instruments may also include a displacement transducer, a positional sensor, and/or orientation sensor 186 in some embodiments of the invention. Moreover, one or more instruments may include a marker 189 to assist in acquisition and tracking of the instruments.

Additional information about a teleoperation medical system is provided in U.S. Patent Application Pub. No. 2012/0020547, published Jan. 26, 2012.

Endoscopic Imager System

Figure 7A:
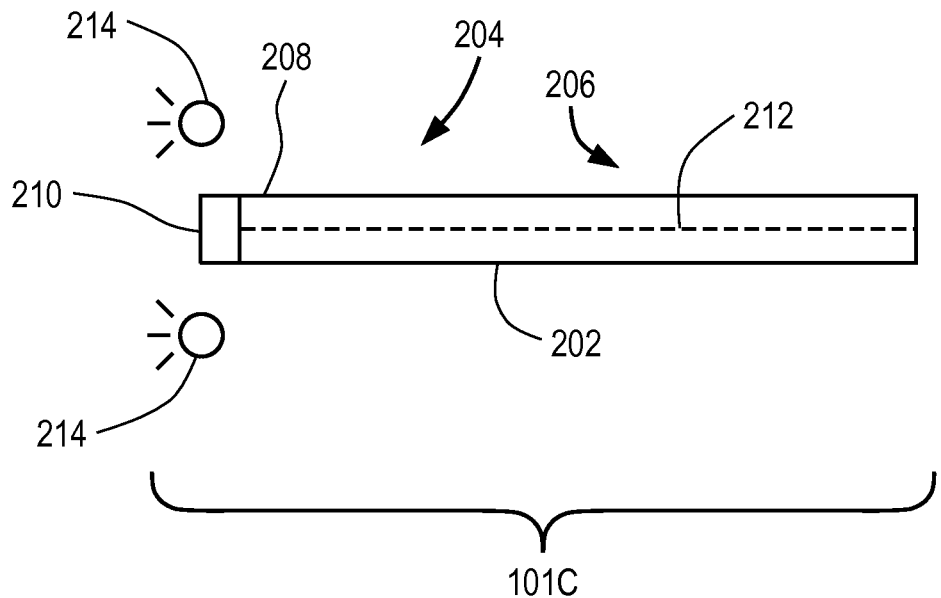
FIG. 7A is an illustrative drawing of a first image capture system in accordance with some embodiments.

FIG. 7A is an illustrative drawing of a first image capture system 101C in accordance with some embodiments. The image capture system 101C includes an endoscope that includes elongated portion 202, which includes a first end portion 204 and a second end portion 206 and a tip portion 208 of the first end portion 204. The first end portion 202 is dimensioned to be inserted into a human body cavity. An imager sensor array 210, which includes multiple image sensors (not shown), is to the tip portion 208 of the first end portion 204. The elongated portion 202 has a length sufficient to position the tip portion 208 close enough to a target object within the body cavity that the object can be imaged by the imager sensor 210. In accordance with some embodiments, the second end portion 206 may include physical contours and/or structures (not shown), as generally described above, so as to securely interfit with a mechanical arm (not shown). The elongated portion 202 also one or more electronic signal paths 212 to electronically communicate information with the imager sensor array 210. A light source 214 is disposed to illuminate the object to be imaged. In accordance with some embodiments, the light source 214 can be unstructured light, white light, color filtered light or light at some selected wavelength, for example.

Figure 7B:
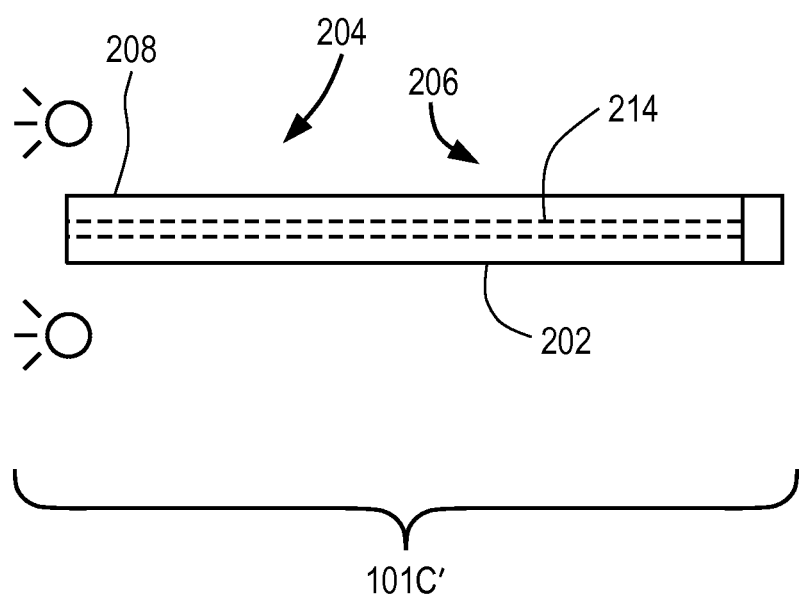
FIG. 7B is an illustrative drawing of a second image capture system in accordance with some embodiments.

FIG. 7B is an illustrative drawing of a second image capture system 101C', in accordance with some embodiments. Aspects of the second image capture system 101C' that are essentially the same as those of the first image capture system 101C are indicated by identical reference numerals and are not described again. An input to a light pipe input, such as a rod lens, is disposed at the tip portion 208 of the first end portion 204. A light pipe body extends within the elongate portion 202 so as to transmit an image received as the light pipe input to the imager sensor array 210, which is physically displaced from the tip portion 208. In some embodiments, the imager sensor is displaced far enough from the tip portion 208 that the sensor array 210 is located outside the body cavity during observation of objects within the cavity.

Figure 8:
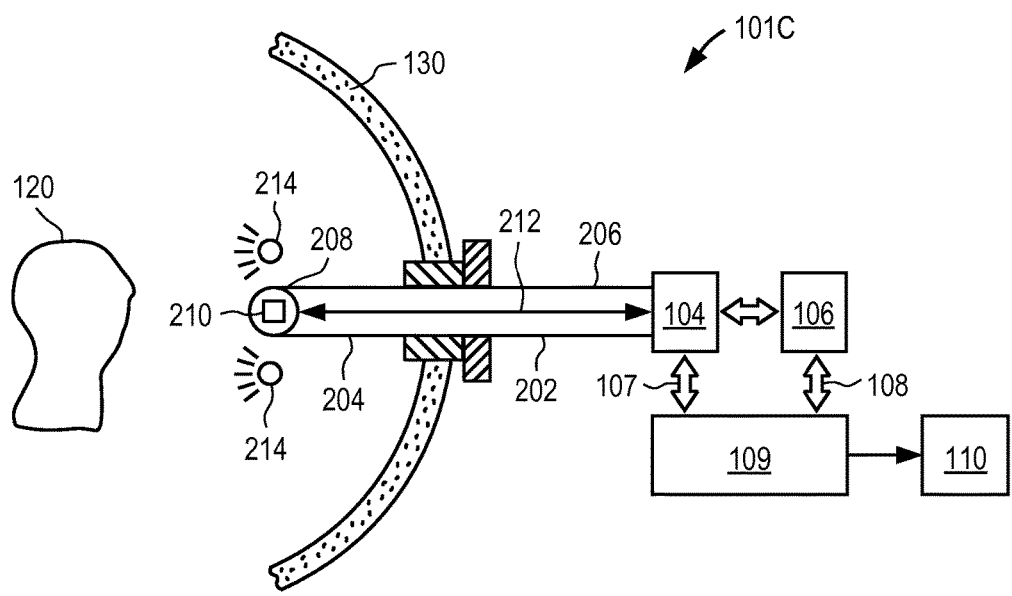
FIG. 8 is illustrative block diagram showing control blocks associated with the first image capture system of FIG. 7A and showing the system in operation, in accordance with some embodiments.

FIG. 8 is illustrative block diagram showing control blocks associated with the first image capture system 101C of FIG. 7A and showing the system 101C in operation, in accordance with some embodiments. Images captured by the imager sensor array 210 are sent over a data bus 212 to a video processor 104, which communicates via bus 105 with a controller 106. The video processor 104 may comprise a camera control unit (CCU) and a video signal detector (VSD) board. The CCU programs or controls various settings of the imaging sensor 210, such as brightness, color scheme, white balance, etc. The VSD processes the video signal received from the imaging sensor.

In accordance with some embodiments a processor system that includes one or more than one processor is configured to perform processor functions. In some embodiments the processor system includes multiple processors configured to operate together to perform the processor functions described herein. Thus, reference herein to at least one processor configured to perform one or more functions includes a processor system in which the functions may be performed by one processor alone or by multiple processors working together.

Alternatively, the CCU and VSD could be integrated into one functional block. In one implementation, the controller 106, which includes a processor and a storage device (not shown) computes the physical quantitative 3D coordinates of the points in a scene adjacent the tip 208 of the elongated portion and drives both the video processor 104 and a 3D display driver 109 to compose3D scenes, which then can be displayed on a 3D display 110. Data buses 107 and 108 exchange information and control signals among the video processor 104, the controller 106 and the display driver 109. In some embodiments, these elements can be integrated with the image sensor array 210 inside the body of endoscope 202. Alternatively, they can be distributed internally and/or externally to the endoscope. The endoscope 202 is shown positioned, via a cannula 140, to penetrate body tissue 130 in order to provide visualize access to a surgical scene that includes a target 120. The target 120 can be an anatomic target, another surgical instrument or any other aspect of the surgical scene inside a patient's body.

Example of Q3D Information Added to an Image of a Scene

Referring once again to FIG. 4 is an illustrative drawing showing a perspective view of a viewer 312 of the master control console 150 of FIG. 5 in accordance with some embodiments. In accordance with some embodiments, to provide a three-dimensional perspective, the viewer 312 includes stereo images for each eye including a left image 400L and a right image 400R of the surgical site including any instruments 400 and a target 410 respectively in a left viewfinder 401L and a right viewfinder 401R. The images 400L and 400R in the viewfinders may be provided by a left display device 402L and a right display device 402R, respectively. The display devices 402L, 402R may optionally be pairs of cathode ray tube (CRT) monitors, liquid crystal displays (LCDs), or other type of image display devices (e.g., plasma, digital light projection, etc.). In the preferred embodiment of the invention, the images are provided in color by a pair of color display devices 402L, 402R; such as color CRTs or color LCDs. To support backward compatibility with existing devices, stereoscopic display devices 402L and 402R may be used with a Q3D system. Alternatively, the Q3D imaging system can be connected to 3D monitors, 3D TVs, or to autostereoscopic displays, such as a display that does not require use of 3D effect eye glasses.

A viewing system having two imaging elements 206R, 206L can provide a good 3D viewing perspective. The Q3D imaging system supplements this viewing perspective with physical dimension information for physical structures in the surgical scene. The stereo viewer 312 used in conjunction with a Q3D endoscopy system, can display Q3D information overlayed onto the stereo image of the surgical scene. For example, as shown in FIG. 4, the numerical Q3D distance value "d_Instr_Trgt" between instrument 400 and target 410 can be displayed within stereo viewer 312.

An explanation of a video stereo viewing system that can be used to overlay physical location and dimension information onto a 3D perspective of a surgical scene is provided in U.S. Patent Application Pub. No. 2012/0020547, paragraphs [0043]-[0053] and corresponding drawings are expressly incorporated herein by their reference.

Processing Quantitative Three-Dimensional Physical Information

Figure 9:
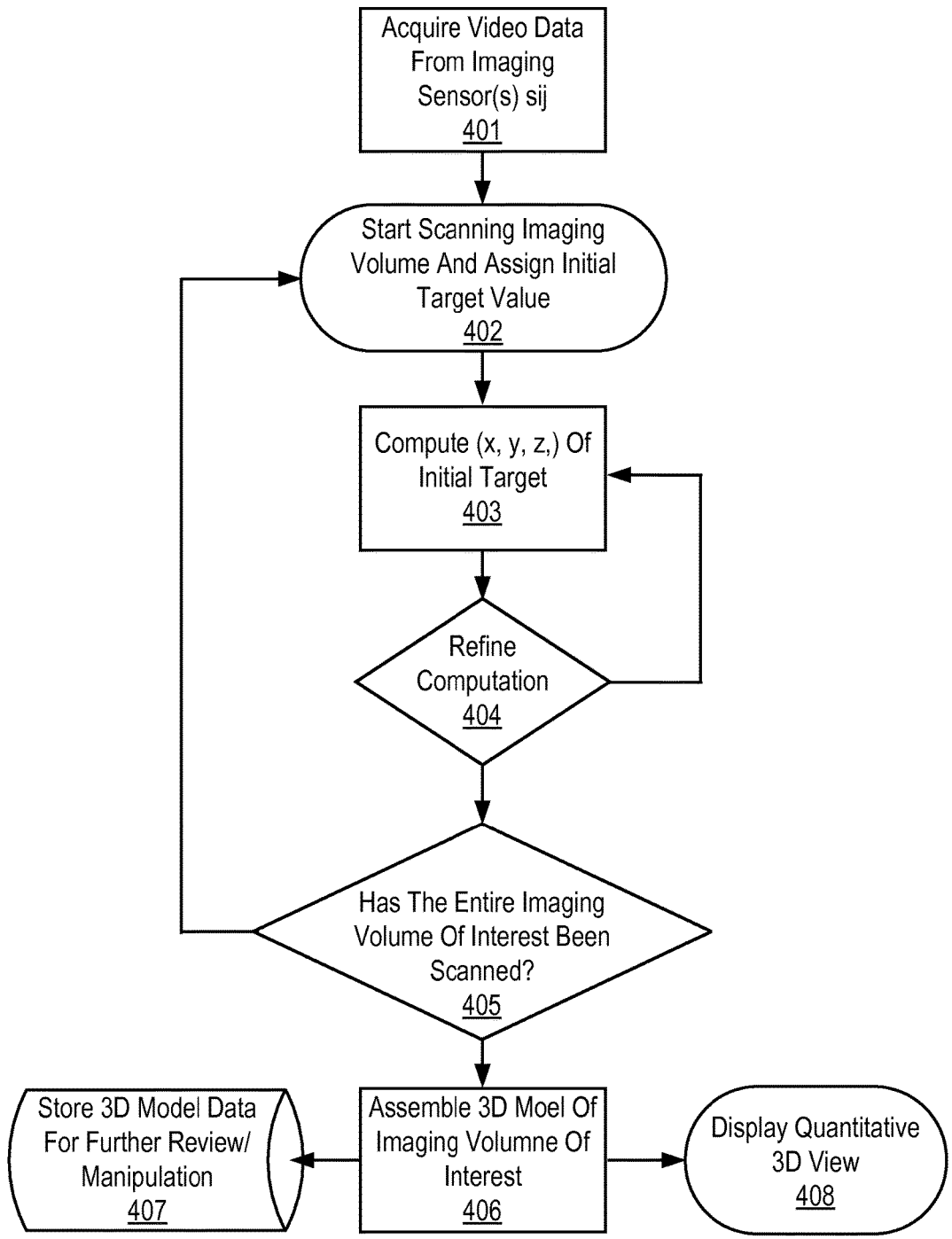
FIG. 9 is an illustrative flow diagram representing a process to determine a quantitative three dimensional location of a physical target in accordance with some embodiments.

FIG. 9 is an illustrative flow diagram representing a process to determine a quantitative three dimensional location of a physical target in accordance with some embodiments. The process is described with reference to the Q3D system 101C of the embodiment of FIG. 8 Module 401 configures the controller 106 to acquire video data from imaging sensors $S_{ij}$. It will be appreciated that although the image sensor array 210 "images" an entire field of view, different sensors and different pixels within different sensors may be illuminated by image projections from different object points within the field of view. The video data, for example, may include color and light intensity data. Each pixel of each sensor may provide one or more signals indicative of the color and intensity of an image projected onto it. Module 402 configures the controller to systematically select targets from a selected region of interest in a physical world view. Module 403 configures the controller to commence the computation of the target 3D coordinates (x, y, z) with an initial ($x_0$, $y_0$, $z_0$) set. The algorithm then checks the coordinates for consistency, by using image diversity data from all sensors Sij that see the target. The coordinate computation is refined at step 404 until an acceptable accuracy is reached. Decision module 404 configures the controller to determine whether the currently computed physical location is sufficiently accurate. In response to a determination that the currently computed location is not accurate enough, control flows back to module 403 to try a different possible physical location. In response to a determination that the currently computed location is sufficiently accurate, module 405 configures the controller to determine whether the entire region of interest has been scanned. In response to a determination that the entire region of interest has not been scanned, control flows back to module 402 and a different target is selected. In response to a determination that the entire region of interest has been scanned, control flows module 406 configures the controller to assemble a three-dimensional model of the imaging module of interest. Assembly of a 3D image of a target based upon from three-dimensional information indicating the physical position of structures of the target is known to persons of ordinary skill in the art and need not be described herein. Module 407 configures the controller to store the 3D model developed using the physical position information determined for multiple targets for further review and manipulation. For example, the 3D model could be used at a later time for surgical applications such as sizing an implant for the particular dimensions of a patient's organ. In yet a different example, when a new surgical instrument 101 is installed on the robotic system 152 it may be necessary to call back the 3D model and display it on monitor 110 in order to reference the new instrument to the previous surgical scene. Module 408 configures the controller to use the physical position information determined for multiple targets to display a quantitative 3D view. An example of a Q3D view is the distance value "d_Instr_Trgt" shown in FIG. 4.

Figure 10:
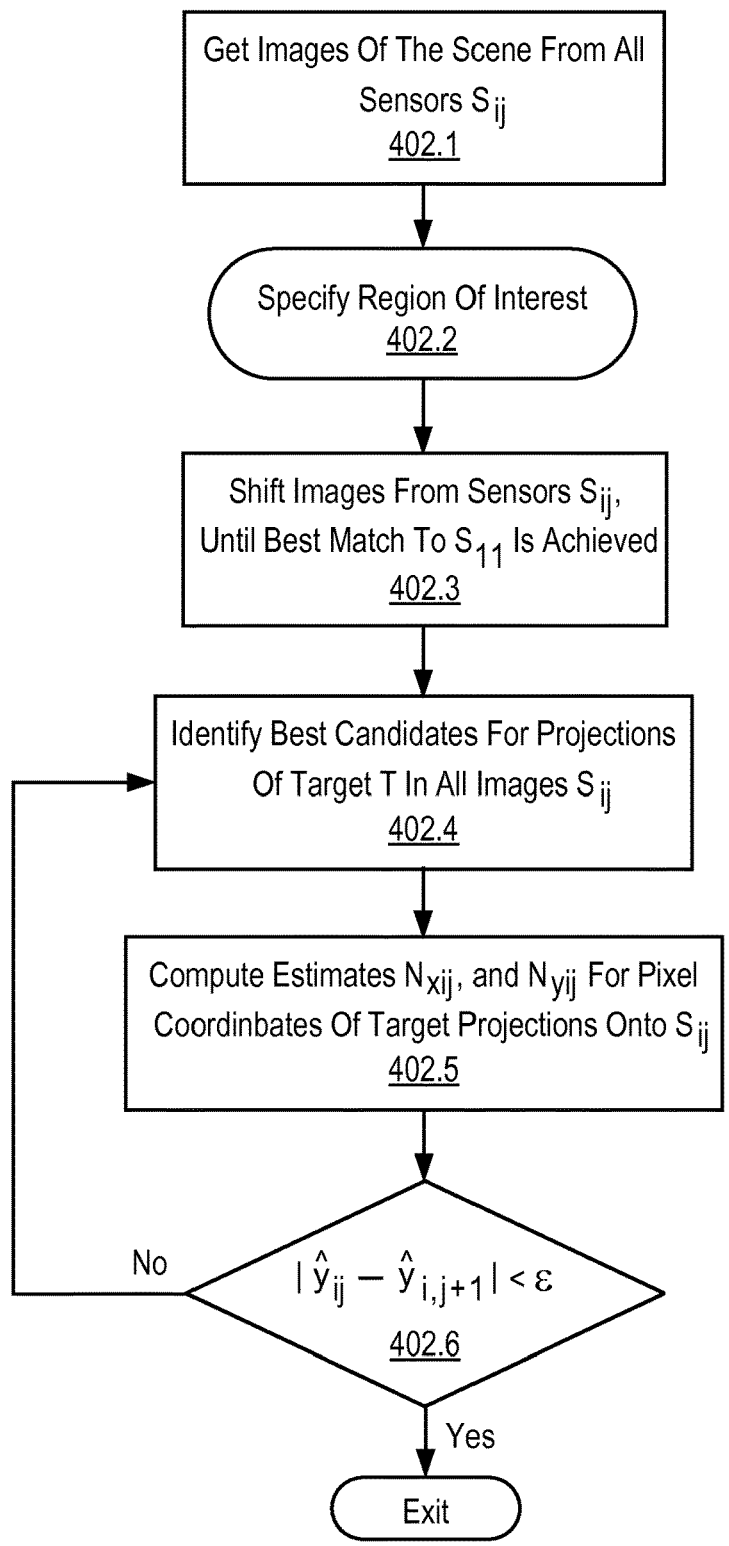
FIG. 10 is an illustrative flow diagram showing certain details of a process generally corresponding to module FIG. 9 to systematically select targets in accordance with some embodiments.

FIG. 10 is an illustrative flow diagram showing certain details of a process generally corresponding to module 402 of FIG. 9 in accordance with some embodiments. Module 402.1 configures the controller to capture images of a physical world scene from all sensors in the sensor array 210. Module 402.2 configures the controller to specify a region of interest from within the captured scene. Module 402.3 configures the controller to search for a best match as between scene images within the region of interest so as to identify pixel locations in different sensors that are illuminated by projections of the same target. As explained later, the best matching may be achieved, without limitation, by shifting the individual images from sensors $S_1$ until maximizing two-dimensional cross-correlation function between the shifted image and a reference image. The reference image, for example, may be the scene image received from sensor $S_{11}$. Module 402.4 configures the controller to identify candidate pixels illuminated by projections from the same target. Module 402.5 configures the controller to compute two or more pixel coordinates ($N_x$, $N_y$) coordinates for the selected target to determine whether the candidate pixels are illuminated by a projection from the same target. Decision module 402.6 determines whether the computed 2D pixel coordinate values indicate that the candidate pixels are illuminated by a projection from the same target. The image diversity caused by viewing the same scene with multiple sensors $S_{ij}$ plays a role in correctly identifying ($N_x$, $N_y$) associated with a specific target in the various individual images $S_{ij}$. For example, in accordance with some embodiments, assuming a simplified scenario where only three sensors are used, $S_{11}$, $S_{12}$ and $S_{13}$, if the triplet of 2D pixel coordinates [($Nx_{11}$, $Ny_{11}$), ($Nx_{12}$, $Ny_{12}$), ($Nx_{13}$, $Ny_{13}$)] are not corresponding to projections of the same target onto [$S_{11}$, $S_{12}$ and $S_{13}$] then the quantities $\hat{y}_{12}$ and $\hat{y}_{13}$ (which are estimates of the projection shift in the y direction) will yield different values. According the equations presented later, $\hat{y}_{12}$ and $\hat{y}_{13}$ should be equal if pixel coordinates ($Nx_{11}$, $Ny_{11}$), ($Nx_{12}$, $Ny_{12}$), ($Nx_{13}$, $Ny_{13}$) come from projections of the same target.

$$\hat{y}_{12} = \frac{Ny_{11}}{Ny_{11} - Ny_{12}} \quad (402.5\text{-}1)$$

$$\hat{y}_{13} = 2 \cdot \frac{Ny_{11}}{Ny_{11} - Ny_{13}} \quad (402.5\text{-}2)$$

If $\hat{y}_{12}$ and $\hat{y}_{13}$ are not approximately equal then control flows back to module 402.4 and to refine the best candidates for target projections onto sensor planes $S_{ij}$. As mentioned, the above is just a simplified implementation of the algorithm. In general, as shown in FIG. 10 module 402.6, the norm of the difference between $\hat{y}_{i,j}$ and $\hat{y}_{i,j+1}$ should be less than an acceptable tolerance ε in order for module 402 to complete its iterations. A similar restriction should be met for the corresponding estimates for the x axis, $x_{i,j}$ and $x_{i,j+1}$. In response to a determination that the computed 2D pixel coordinate values ($N_x$, $N_y$) do indicate that the candidate pixels are illuminated by a projection from the same target, then control flows to module 403.

It will be appreciated that each pixel directly captures color and intensity information from a world scene. Moreover, in accordance with the above process, each pixel is associated with the (x, y, z) coordinates of the physical object in the world view that is projected onto the pixel. Thus, color information, illumination intensity information and physical location information, i.e. the location of the physical object that projected the color and illumination, can be associated with a pixel in a non-transitory computer readable storage device. The following Table 1 illustrates this association.

TABLE 1

| Pixel Identifier | Color Value | Intensity Value | Location (x, y, z) |
| --- | --- | --- | --- |

Examples of Determining Q3D Information

Example of Projection Matching

Figure 11:
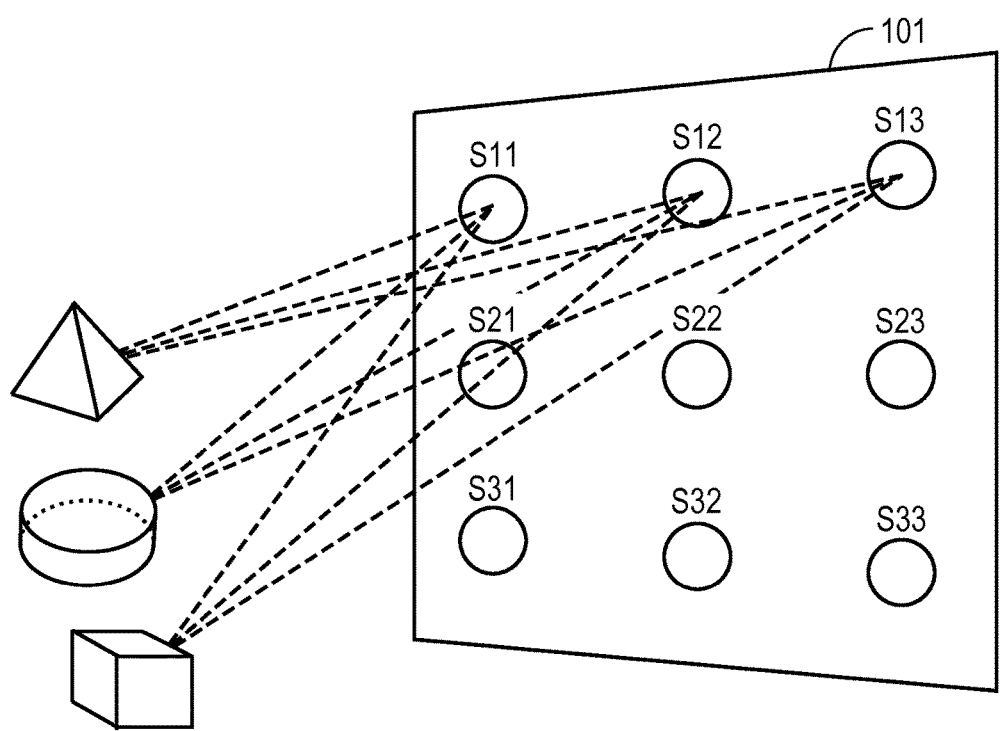
FIG. 11 is an illustrative drawing of an example sensor imager array that includes multiple sensors and that is disposed to have a field of view that encompasses an illustrative three dimensional physical world scene that includes three illustrative objects in accordance with some embodiments.

FIG. 11 is an illustrative drawing of an example sensor imager array 210 that includes multiple sensors $S_{11}$-$S_{33}$ that is disposed to have a field of view that encompasses an illustrative three dimensional physical world scene that includes three illustrative objects in accordance with some embodiments. Each sensor in the array includes a two dimensional arrangement of pixels having at least two pixels in each dimension. Each sensor includes a lens stack that creates a separate optical channel that resolves an image onto a corresponding arrangement of pixels disposed in a focal plane of the lens stack. Each pixels act as a light sensor and each focal plane with its multiple pixels acts as an image sensor. Each sensor $S_{11}$-$S_{33}$ with its focal plane occupies a region of the sensor array different from regions of the sensor array occupied by other sensors and focal planes. Suitable known image sensor arrays are disclosed in U.S. Pat. No. 8,514,491 and in U.S. Patent Application Pub. No. 20013/0070060, which are described above.

In accordance with some embodiments, the sensors are characterized by a $N_x$ and $N_y$, their total number of pixels in the x and y directions, and by field of view angles, $\theta_x$ and $\theta_y$. In some embodiments, the sensor characteristics for the x and y axes are expected to be the same. However, in alternative embodiments, the sensors have asymmetric x and y axes characteristics. Similarly, in some embodiments, all sensors will have the same total number of pixels and the same field of view angle. The sensors are distributed across the array 210 in a well-controlled manner. For example, the sensors may be at δ distance apart on the two-dimensional grid shown. The sensor placement pitch δ may be symmetric or asymmetric across such grid.

In the embodiment shown in FIG. 11, the sensors are arranged in a rectangular grid in which sensors $S_{11}$-$S_{13}$ occupy a top row, sensors $S_{21}$-$S_{23}$ occupy a middle row, and sensors $S_{31}$-$S_{33}$ occupy a bottom row. Each sensor includes N rows of pixels and N columns of pixels. Light rays, indicated by dashed lines, produced by a light source are reflected from each of a triangle shaped first object, a spherical shaped second object and a rectangular shaped third object, to each sensor of the imager array. For illustration purposes, only rays to sensors $S_{11}$, $S_{12}$ and $S_{13}$ in the top row are shown. The light source may be non-structured white light or ambient light, for example. Alternatively, the light source may provide light at a selected wavelength such as infrared, or may be filtered or split to provide a selected color or range of colors, for example. It will be appreciated that light rays are similarly reflected from each of the objects to sensors $S_{21}$-$S_{33}$. However, in order to simplify the explanation, these other light rays are not shown.

Figure 12:
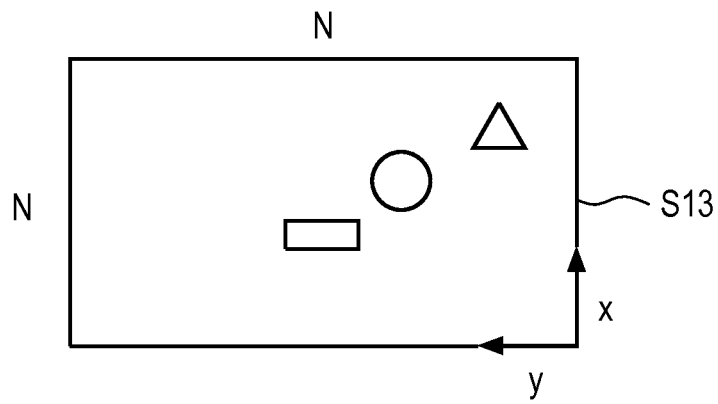
FIG. 12 is an illustrative drawing representing projections of the multiple physical objects of FIG. 11 onto multiple sensors in accordance with some embodiments.
Figure 12:
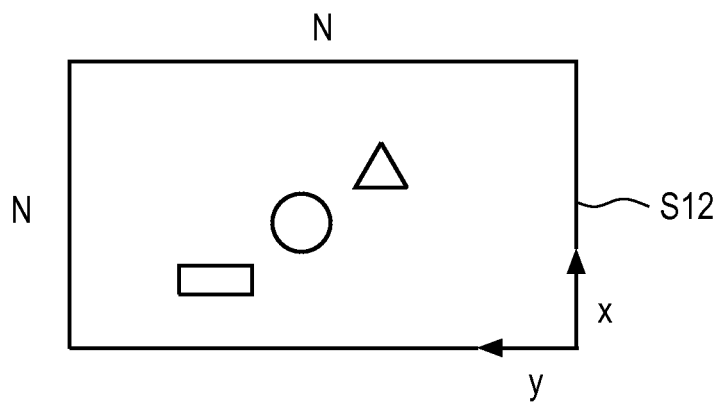
Figure 12:
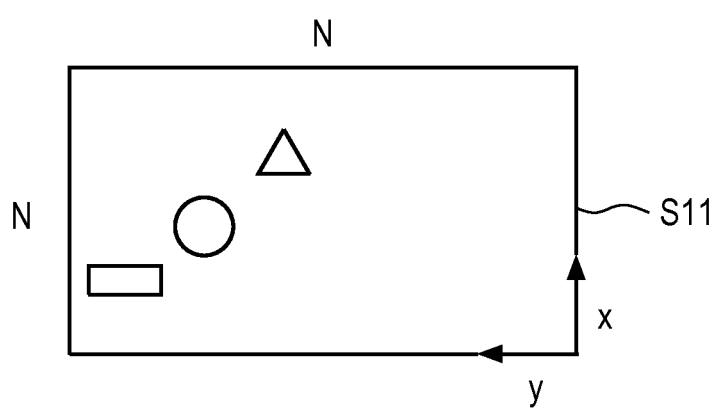

In accordance with modules 401 and 402.1, sensors of the array separately capture images from a world view, and in accordance with module 402.1. FIG. 12 is an illustrative drawing representing projections of the three objects of FIG. 11 onto the sensors $S_{ij}$ (only $S_{11}$, $S_{12}$ and $S_{13}$ shown) in accordance with some embodiments. A person of ordinary skill in the art will appreciate that the reflected light rays incident upon that sensors project images of the objects that are in the field of view. More specifically, the rays of light reflected from the objects in the field of view that are incident upon multiple different image sensors of the imager array produce multiple perspective projections of the objects from three-dimensions to two dimensions, i.e. a different projection in each sensor that receives the reflected rays. In particular, the relative location of projections of the objects is shifted from left to right when progressing from $S_{11}$ to $S_{12}$ to $S_{13}$. Image sensor pixels that are illuminated by incident light rays produce electrical signals in response to the incident light. Accordingly, for each image sensor, a pattern of electrical signals is produced by its pixels in response to the reflected rays that indicates the shape and location of the image projection within that image sensor.

Figure 13:
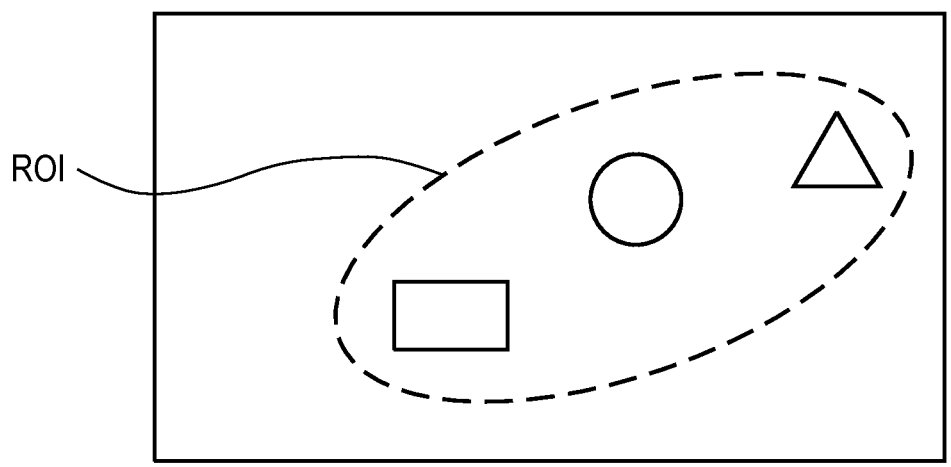
FIG. 13 is an illustrative drawing indicating selection of a region of interest from within a real-world scene in accordance with some embodiments.

In accordance with module 402.2, a region of interest is selected from the world scene. FIG. 13 is an illustrative drawing indicating selection of a region of interest from within the scene. In this example, the triangle shaped first object, spherical shaped second object and rectangular shaped third object all are in the selected region of interest. This step can be achieved by accepting input from an operator, or it can be automatically performed using a computer configured by software in a prescribed manner, or by combination of operator inputs and automatic software-controlled selection. For example, in some embodiments, the world scene may show an internal cavity of the human anatomy and the objects may be internal body organs or surgical instruments or portions thereof. A surgeon may receive real time visual imagery from within the internal cavity and may have within her field of view tissue regions of the human anatomy and a portion of the surgical instruments projecting within the body cavity. The surgeon may specify those objects within the field of view for which location information is to be determined through well-known techniques such as a video marker such as telestration, for example. Alternatively or in addition to such operator request, an automated process such as an edge detection algorithm can be used to specify a region of interest (ROI).

Figure 14:
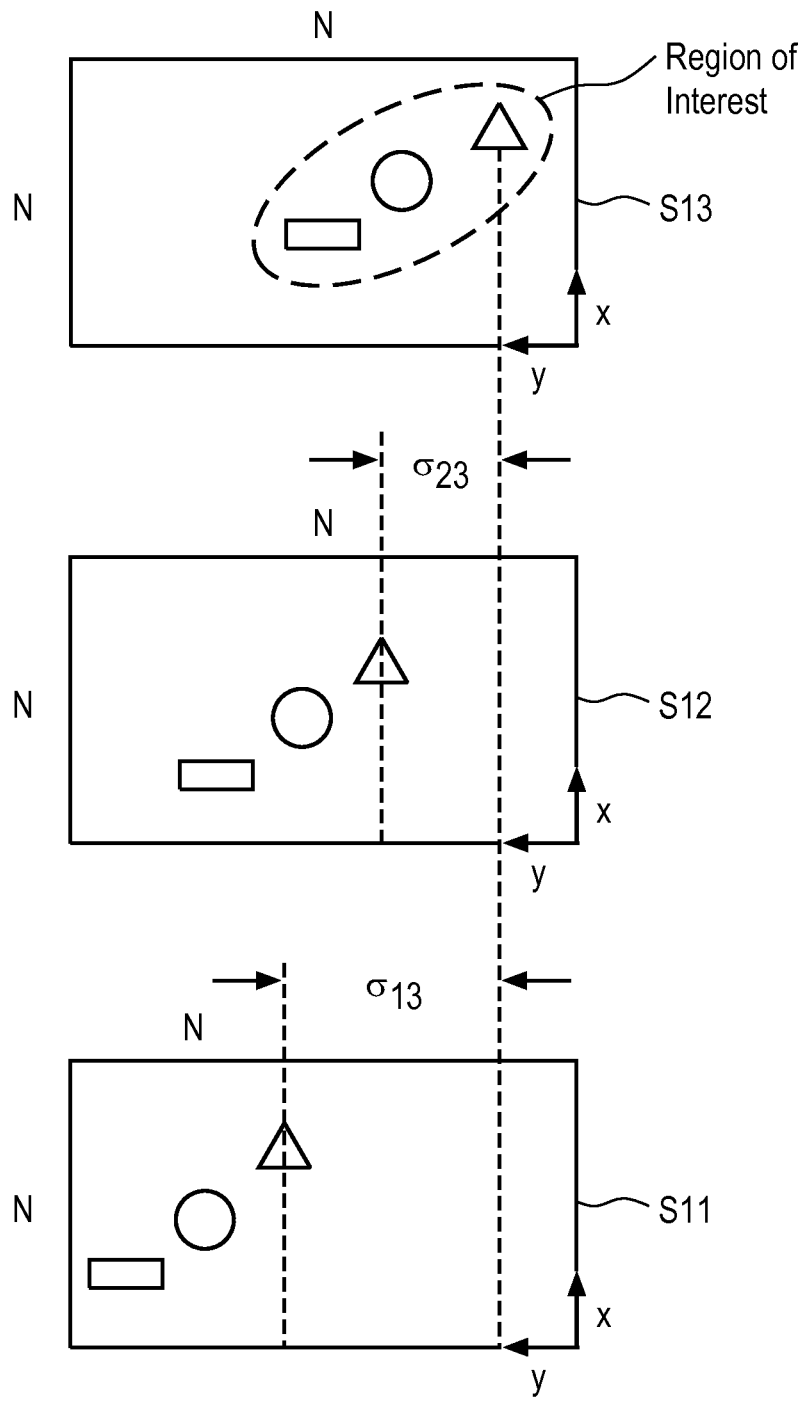
FIG. 14 is an illustrative drawing showing detail as to relative geometric offset of the projected images in sensors multiple sensors in accordance with some embodiments.

In accordance with module 402.3, a best match is determined as between scene images within the region of interest so as to identify pixel locations in different sensors that are illuminated by projections of the same target. FIG. 14 is an illustrative drawing showing additional detail as to relative geometric offset of the projected images in sensors $S_{11}$, $S_{12}$ and $S_{13}$ in accordance with some embodiments. In accordance with some embodiments, an image from sensor $S_{13}$ is considered to be reference image, the projections of the objects in the selected ROI are offset to the right by an amount $\sigma_{23}$ pixels in sensor $S_{12}$ relative to their location in sensor $S_{13}$. The projections of the objects in the selected ROI are offset to the right by an amount $\sigma_{13}$ pixels in sensor $S_{11}$ relative to their location in sensor $S_{13}$.

Figure 15:
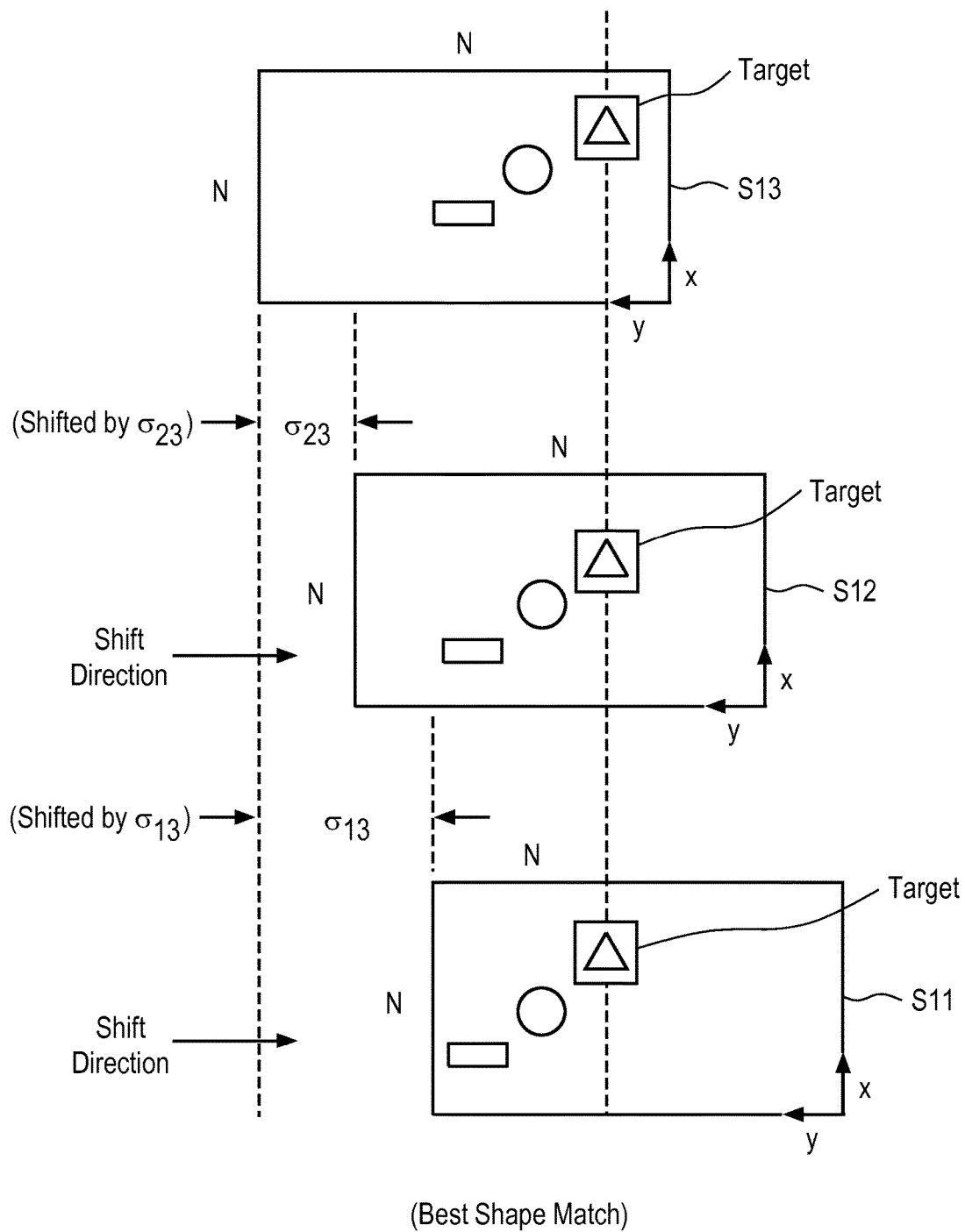
FIG. 15 is an illustrative drawing showing the projected images in certain example sensors within the region of interest (ROI) shifted to the right to align with the projected images in a designated reference sensor within the ROI in accordance with some embodiments.

FIG. 15 is an illustrative drawing showing the projected images in sensors $S_{11}$ and $S_{12}$ within the ROI shifted to the right to align with the projected images in sensor $S_{13}$ within the ROI in accordance with some embodiments. In the current example, sensor $S_{13}$ is designated to act as a reference sensor. It will be appreciated that other sensors can be chosen for use in determining alignment and geometric dimensions. Projections of the objects within the selected ROI are identified in the designated sensor, e.g., sensor $S_{13}$, and projections in the other sensors, e.g., in sensors $S_{11}$ and $S_{12}$, are shifted until they align with the projection in the designated sensor. In this manner, the corresponding projections of objects within the selected ROI can be identified within the other sensors, together with their offsets relative to the location of the projections in the designated sensor.

In particular, for example, the projections of the three example objects are shifted to the right by an amount $\sigma_{23}$ pixels in sensor $S_{12}$, and the projections of the three example objects are shifted to the right by an amount $\sigma_{13}$ pixels in sensor $S_{13}$. In this illustrative example, in order to simplify the explanation, it is assumed that the projections are offset in the y direction only and not in the x direction, although the same principles apply for x direction projection offsets as between sensors. Moreover, although this example shows a linear offsets, a person of ordinary skill in the art can apply other transformations such as rotation, for example, to align projections that have relative offsets in different sensors.

In accordance with some embodiments for example, two-dimensional (2D) cross-correlation techniques or principal component analysis (PCA), can be used to align the projections within the ROI in $S_{13}$ with the projections within the ROI in $S_{12}$ and to align the projections within the ROI in $S_{13}$ with the projections within the ROI in $S_{11}$. In general, the intent is to best match or align the images from sensors $S_{ij}$ with respect to the image from the sensor designated as reference. More specifically, the projected images within the ROI in $S_{12}$ are shifted and cross-correlated with the projected images within the ROI in $S_{13}$ until a highest correlation coefficient is achieved. Likewise, the projected images within the ROI in $S_{11}$ are shifted and cross-correlated with the projected images within the ROI in $S_{13}$ until a highest correlation coefficient is achieved. Thus, alignment of the projections of the ROI is used to identify the locations of the projections of the ROI in sensors $S_{11}$ and $S_{12}$ by determining the offset between the projection of the ROI in $S_{13}$ and the projection of the ROI in $S_{12}$ and by determining the offset between the projection of the ROI in $S_{13}$ and the projection of the ROI in $S_{11}$.

Example of Candidate Pixel Selection and Refinement

In accordance with module 402.4, candidate pixels are identified within different sensors, which according to the best match process, are illuminated by projections from the same target. Once the projections of objects within the ROI have been identified in each of the sensors $S_{11}$, $S_{12}$ and $S_{13}$, the physical (x, y, z) projections of individual target points within the ROI can be determined relative to the imager array. In accordance with some embodiments, for each of a multiplicity of target points within the ROI, one or more pixels within each of multiple sensors is identified that is illuminated by a projection from the target point. For each such target point, a physical (x, y, z) target point location is determined based at least in part upon the geometric relationships among pixels disposed in different sensors that are determined to be illuminated by projections from the target point.

It will be appreciated that a sequence of target points can be chosen automatically by systematically traversing the ROI (e.g., right to left with a certain step size and up to down with a step size), and a physical (x, y, z) target point location can be determined for each selected target point. Since $S_{11}$ and $S_{12}$ are best matched to $S_{13}$, the traversing is performed inside the shifted regions of interest. Selecting a target involves identifying a pixel in each of sensors $S_{11}$, $S_{12}$ and $S_{13}$ that is illuminated by a projection of the target. Thus, candidate pixels in each of $S_{11}$, $S_{12}$ and $S_{13}$ are identified as being the ones illuminated by a projection of the selected target point.

In other words, in order to select a target point T, a pixel is selected in each of the sensors $S_{11}$, $S_{12}$ and $S_{13}$ that is illuminated by a projection of the target point T. It will be appreciated that the (x, y, z) physical location of the target T is unknown at the moment of its selection. Moreover, it will be appreciated that inaccuracy of the above-described alignment process can result in inaccuracy in the determination of which pixels in each sensor are illuminated by the projection of a selected target T. Thus, as explained with reference to FIGS. 17, 18 and 19, a further determination is made as to the accuracy of the determination as to the pixels in each of $S_{11}$, $S_{12}$ and $S_{13}$ that are illuminated by the projection of a currently selected target T.

Figure 16:
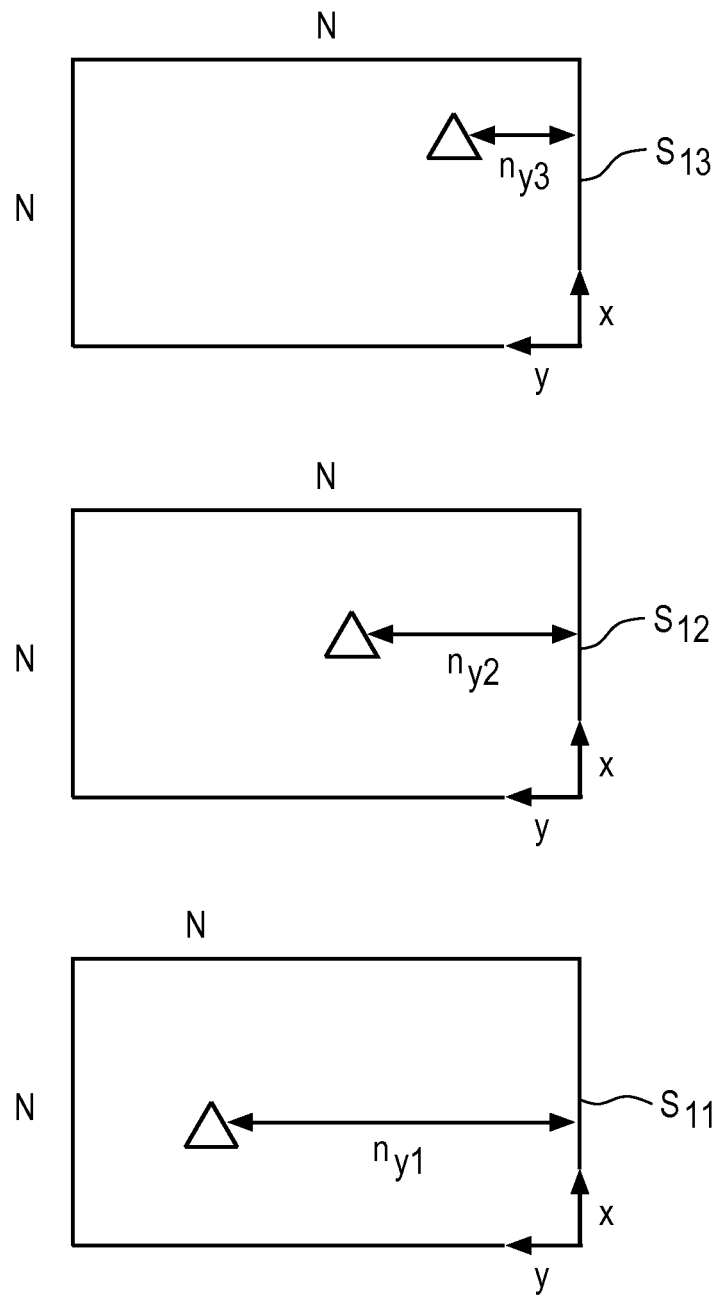
FIG. 16 is an illustrative drawing showing projections of a selected target point onto multiple sensors in accordance with some embodiments.

Continuing with the above example, assume that the triangle shaped first object is the currently selected target point. FIG. 16 is an illustrative drawing showing projections of the selected triangle shaped target point onto sensors $S_{11}$, $S_{12}$ and $S_{13}$ in accordance with some embodiments. From these projections, the 2D pixel coordinates for target T are determined, $[(Nx_{11}, Ny_{11}), (Nx_{12}, Ny_{12}), (Nx_{13}, Ny_{13})]$. For simplification, FIG. 16 shows only the y-axis pixel coordinates. Using these 2D pixel coordinates, expressions (402.5-1) and (402.5-2) are applied and $\hat{y}_{12}$ and $\hat{y}_{13}$ computed as part of module 402.5. Part of module 402.6, the norm $|\hat{y}_{12}-\hat{y}_{13}|$ is computed and compared to the acceptable tolerance $\varepsilon$. Similarly, the x-axis pixel coordinates and location estimates are computed and compared against acceptable tolerances. If the condition of module 402.6 is met then the process proceeds to module 403. Else, it returns to module 402.4, to further refine target candidates.

Figure 17:
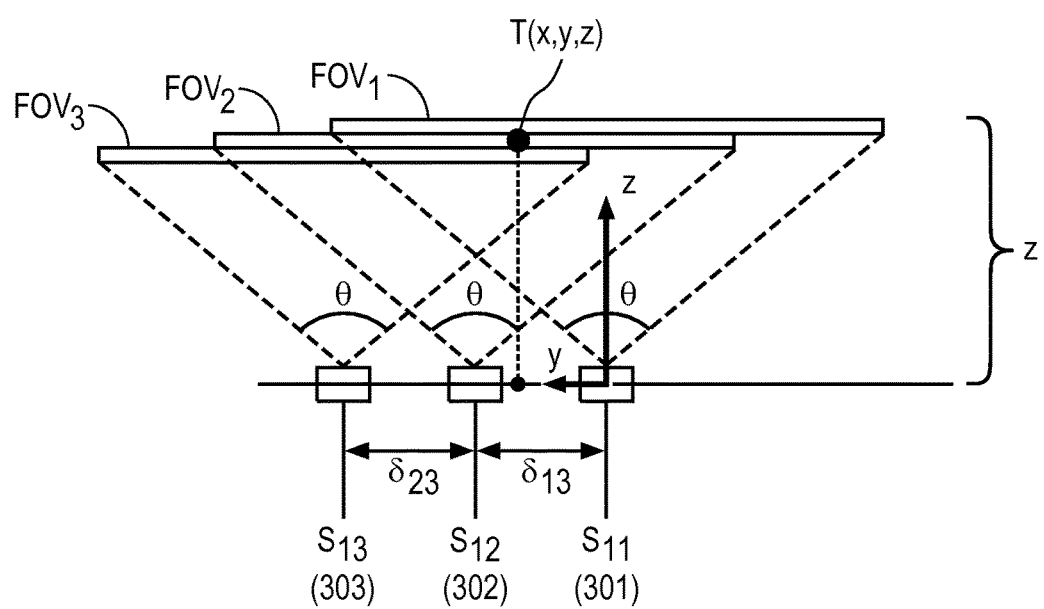
FIG. 17 is an illustrative drawing showing a portion of an imager array that includes the multiple sensors of FIG. 16 and the selected target point T disposed at location in physical space in accordance with some embodiments.

Referring to FIG. 17, there is shown a portion of an imager array that includes sensors $S_{11}$, $S_{12}$ and $S_{13}$ and the selected triangle shaped first object target point T disposed at location (x, y, z) in physical space. Sensors within an imager array have a known spacing between them, $\delta_{ij}$. The physical position spacing between $S_{11}$ and $S_{12}$ is $\delta_{12}$, and the physical position spacing between $S_{12}$ and $S_{13}$ is $\delta_{23}$. In some embodiments these spacing between all sensors $S_{ij}$ is identical, equal to $\delta$, a constructional specification. Sensors $S_{ij}$ also have a known field of view angle $\theta$.

As explained above, in some embodiments, each sensor is constructed as a 2D imaging element with pixels arranged in a rectangular pattern of rows and columns. Alternatively, pixels can be arranged in a circular pattern, zigzagged pattern or scattered pattern or an irregular pattern including sub-pixel offsets, for example. The angle and the pixel characteristics of these elements may be identical or, alternatively, may be different from sensor to sensor. However, these characteristics are assumed to be known. In order to simplify the explanation, it is assumed that the sensors are identical, although they may, however, be different.

For simplicity, let us assume that all sensors $S_{ij}$ have N×N pixels. At a distance z from sensor $S_{11}$, the N-pixel width of the sensor expands out to a y-dimension field of view of $S_{11}$ indicated by $FOV_1$. Likewise, at a distance z from sensor $S_{12}$, the y-dimension field of view of sensor $S_{12}$ is indicated by $FOV_2$. Also, at a distance z from sensor $S_{13}$, the y-dimension field of view of sensor $S_{13}$ is indicated by length $FOV_3$. The lengths $FOV_1$, $FOV_2$ and $FOV_3$ overlap each other, signifying that sensors $S_{11}$, $S_{12}$ and $S_{13}$ achieve a 3-way sampling diversity of target T physically located at some (unknown) distance z. Of course, if the sensors are identically built, as assumed in this example, length $FOV_1$, $FOV_2$ and $FOV_3$ will be identical as well. It will be appreciated that the three lengths $FOV_1$, $FOV_2$ and $FOV_3$ all have the same magnitude and are coplanar in that they are at the same (unknown) z-distance from the imager array, although for the purpose of illustration they are portrayed as if they were stacked adjacent to each other.

Figure 18:
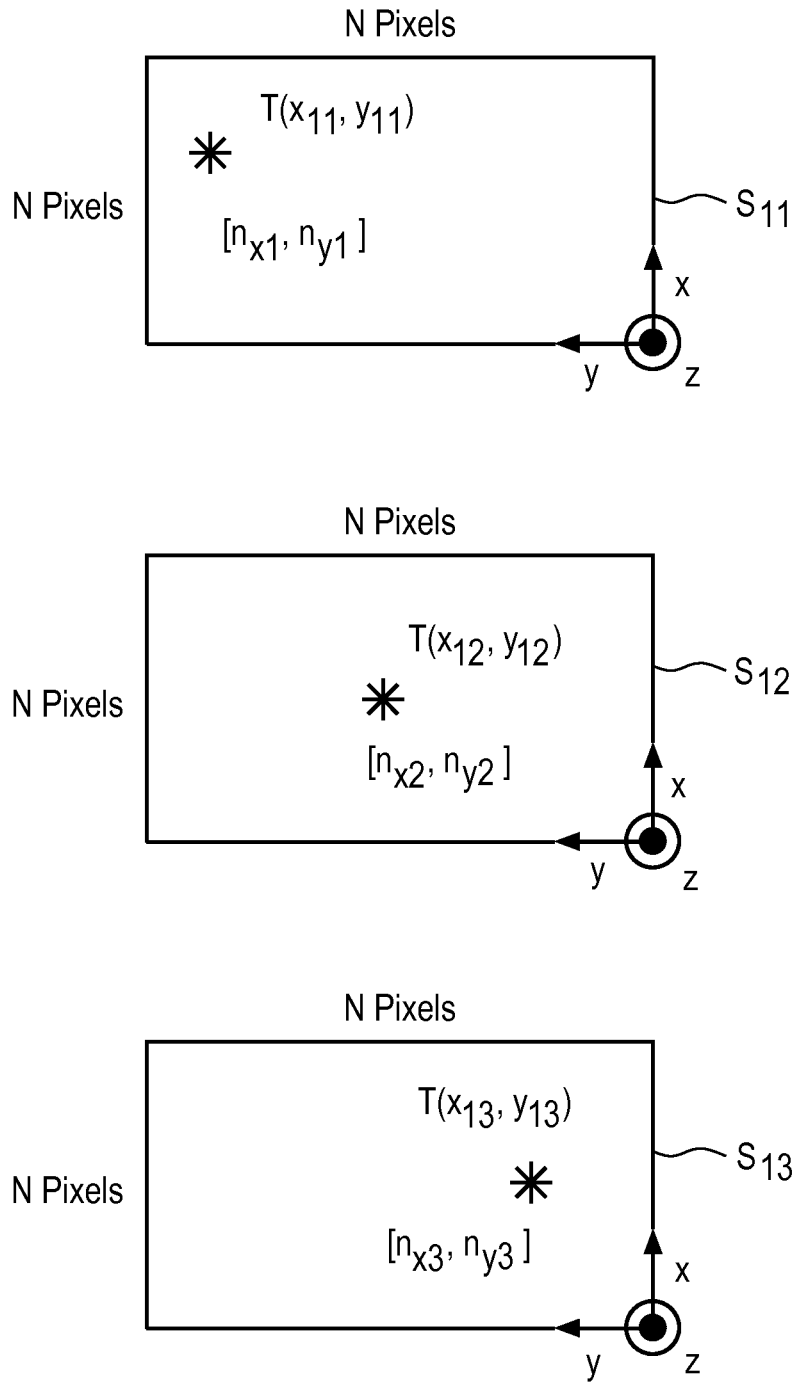
FIG. 18 is an illustrative elevation view of the projection of the currently selected target point T onto the multiple image sensors of FIG. 16 in accordance with some embodiments.

Referring to FIG. 18, there is shown an illustrative elevation view of the projection of the currently selected target point T onto the image sensors $S_{11}$, $S_{12}$ and $S_{13}$. For the sake of simplicity, it is assumed that the sensors include geometrically rectangular pixel arrays of size N×N pixels. It is also assumed that the x coordinates of the target T projections are all equal. In other words, it is assumed that for the projections of target T onto $S_{11}$, $S_{12}$ and $S_{13}$, $n_{x1}=n_{x2}=n_{x3}$. To simplify the explanation, it is also assumed that the geometric field of view angle θ is the same horizontally as it is vertically, $θ_x=θy$. A person of skill in the art would know how to modify the process presented below so that to compute the x, y and z physical coordinates of target T if any of the above assumptions would change.

Figure 19:
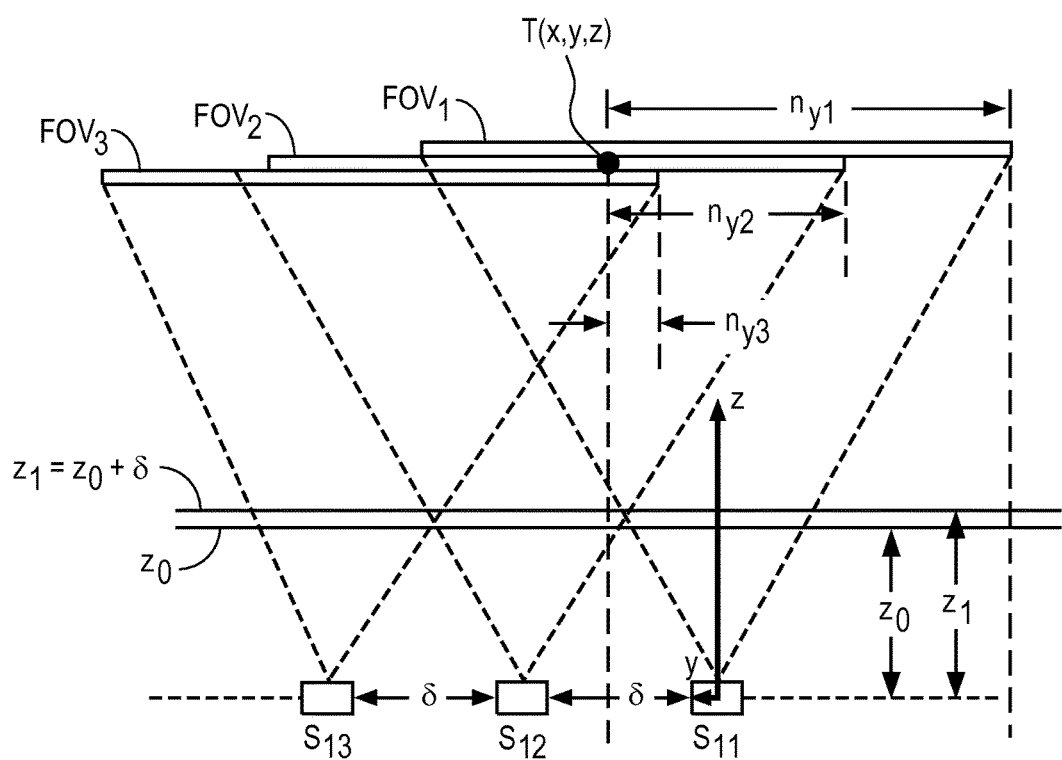
FIG. 19 is an illustrative drawing showing the disposition of a currently selected target relative to the multiple sensors as described above with reference to FIG. 17 and also showing y-direction pixel offsets for the candidate pixel in each of the sensors in accordance with some embodiments.

An image of the target T is projected to a physical point within sensor $S_{11}$ at geometric coordinates $(n_{x1}, n_{y1})$, in the plane of the image sensor $S_{11}$. More specifically, the projection of target point T onto sensor $S_{11}$ is located $n_{y1}$ pixels along the y axis, and $_{nx1}$ pixel along the x axis, taken from the origin. An image of the target T is projected to a physical point within sensor $S_{12}$ at geometric coordinates $(n_{x2}, n_{y2})$, in the plane of the image sensor $S_{12}$. An image of the target T is projected to a physical point within sensor $S_{13}$ at geometric coordinates $(n_{x3}, n_{y3})$, in the plane of the image sensor $S_{13}$. It will be appreciated that pixel locations $(n_{xi}, n_{yi})$ within each sensor are determined relative to origin (0, 0,) reference coordinates provided for the sensor. As shown in FIG. 17 or FIG. 19, a global system of coordinates (x, y, z) is defined and used to reference the target. For example, the origin of such system of coordinates may be placed, without limitations, at the geometrical center of sensor $S_{11}$.

Referring to both FIG. 16 and FIG. 18, it can be seen that the y pixel distance of the projection of the target is different in each sensor. The projection of a currently selected target T is disposed $n_{y1}$ pixels to the left of the origin in $S_{11}$. The projection of the selected target T is disposed $n_{y2}$ pixels to the left of the origin in $S_{12}$. The projection of the selected target T is disposed $n_{y3}$ pixels to the left of the origin in $S_{13}$. As mentioned above, to simplify the explanation, it is assumed that the projection of the target falls at the same x pixel distance from the origin in all three sensors.

Referring to FIG. 19, there is shown the disposition of the currently selected target T relative to sensors $S_{11}$, $S_{12}$ and $S_{13}$ as described above with reference to FIG. 17 and also showing y-direction pixel offsets for the candidate pixel in each of the sensors. It will be understood that the drawings of FIG. 19 present physical structures and an analytical framework for determining the (x, y, z) physical coordinates of the selected target point T. At an (unknown) distance z from the imager array plane, the y-direction field of view for each sensor extends over a length marked as $FOV_i$. This length, $FOV_i$, corresponds to the maximum pixel width of the sensor, which is N pixels, in some embodiments. Given that the working assumption was that the sensor has a field of view that is symmetric in the x and y directions, the length would also be $FOV_i$ vertically, along the x axis.

Recall that the candidate pixel selections are made based at least in part upon a correlation process that can have a level of uncertainty than can result in inaccuracy in determination of the physical location of the selected target. Thus, a further check of the accuracy of the target projection candidate selections, in accordance with some embodiments, is made as follows.

Example of Determining Target's Physical (x, y) Location and Checking Accuracy of Target Projection Candidate Selection In accordance with module 402.5, two or more two-dimensional $(N_y, N_y)$ coordinate values are computed for the selected target to determine whether the candidate pixels actually are illuminated by a projection from the same target. Based on the assumptions discussed above and placing the origin of the 3D system of coordinates at the center of sensor $S_{11}$, the imager array and currently selected target T in the example in FIG. 19 have the following relationships:

$$z = \frac{N \cdot \delta}{2 \cdot (n_{y1} - n_{y2}) \cdot \tan\left(\frac{\theta}{2}\right)} \quad (1)$$

$$y = \frac{2n_{y1} - N}{2(n_{y1} - n_{y2})} \cdot \delta \quad (2)$$

$$x = \left(\frac{2n_{x1}}{N} - 1\right) \cdot z \cdot \tan\left(\frac{\theta}{2}\right) \quad (3)$$

Where:
N is the pixel dimension of the imaging sensors;
$n_{x1}$ is the position of a target point T expressed in number of pixels from the origin of the $S_{11}$ plane in the x direction;
$n_{y1}$ is the position of the target point T expressed in number of pixels from the origin of the $S_{11}$ plane in the y direction;
$n_{x2}$ is the position of a target point T expressed in number of pixels from the origin of the $S_{12}$ plane in the x direction;
$n_{y2}$ is the position of the target point T expressed in number of pixels from the origin of the $S_{12}$ plane in the y direction;
θ is the angle of the field of view.

Moreover, if performing the same math using sensors $S_{11}$ and $S_{13}$ and given that the separation between $S_{11}$ and $S_{13}$ is 2δ, we obtain:

$$z = \frac{2 \cdot N \cdot \delta}{2 \cdot (n_{y1} - n_{y3}) \cdot \tan\left(\frac{\theta}{2}\right)} \quad (4)$$

$$y = \frac{2n_{y1} - N}{2(n_{y1} - n_{y3})} \cdot 2\delta \quad (5)$$

$$x = \left(\frac{2n_{x3}}{N} - 1\right) \cdot z \cdot \tan\left(\frac{\theta}{2}\right) + 2\delta \quad (6)$$

Where:
$n_{x3}$ is the position of a target point T expressed in number of pixels from the origin of the $S_{13}$ plane in the x direction;
$n_{y3}$ is the position of the target point T expressed in number of pixels from the origin of the $S_{13}$ plane in the y direction.

Thus, determination of the physical x coordinate of the selected target T can be determined based upon expressions (3) or (6). A determination of the physical y coordinate of the selected target T can be determined based upon expressions (2) or (5). A determination of the physical z coordinate of the selected target T can be determined based upon equations (1) or (4).

More generally, in accordance with module 402.6, a determination is made as to whether the computed 2D coordinate values indicate that the candidate pixels are illuminated by a projection from the same target. It will be appreciated that a more reliable determination of the physical (x, y, z) coordinates of the target T can be obtained through the use of two formulations for each coordinate. For example, the y coordinate for the target T can be determined using both formulations (2) and (5). If the resulting y coordinate values computed using the two formulations differ by more than some acceptable tolerance value, $\varepsilon_y$, then a determination can be made that the matching process failed to resolve the offset between projections in the different sensors with sufficient accuracy, and as result that the candidate pixels do not correspond in that they do not receive projections from the same target T. In the event of a failure of the y computations to match, another iteration of the matching process may be performed in an effort to make an improved selection of candidate pixels within the sensors that each corresponds to a selected target T. It will be appreciated that the computed y values are unlikely to be equal since the different perspective projections onto different sensors can differ due to parallax effects, for example. Therefore, an acceptable tolerance value is prescribed according to the intended application. For surgical imaging applications, an $\varepsilon$ of 0.1-0.3 mm typically offers an acceptable Q3D accuracy. A person of skill in the art may define different acceptable tolerance levels without departing from the spirit of this invention.

Given the assumed sensor symmetry around the x and y axes, persons skilled in the art will appreciate that the same kind of determination can be made for the x coordinates of the target T using formulations similar to those in (2) and (5), but using $n_{xi}$ instead of $n_{yi}$. Formulations (3) and (6) cannot be used part of 402.5 and 402.6 because they require knowledge of the z coordinate. However, the essence of modules 402.5 and 402.6 is to determine the correct target projections on the planes of sensors $S_{11}$, $S_{12}$ and $S_{13}$. For this purpose formulations (2) and (5), adjusted for x and y axes, are sufficient. The complete set of coordinates (x, y, z) is computed part of modules 403 and 404, as described below.

Example of Determining Target's Physical z Location

As illustrated in FIG. 19, in accordance with modules 403 and 404, an initial estimate for the z coordinate, $z_0$, is used to initiate the computation process. This initial value is defined automatically, according to the medical application. The medical application defines the intended world view to be visualized. The initial value $z_0$ starts at the edge of the field of view closest to the endoscope. Referring to FIG. 8, for a Q3D application involving surgical endoscopy, $z_0$ can be 1-5 mm off the distal end 208 of the Q3D endoscope 202, for example. Such initial estimate generally is sufficient for this application as it is unlikely to have any tissues or surgical instruments reside in such close proximity to the Q3D endoscope. Next, value $z_0$ is plugged into formulations (3) and (6). Given that the x coordinate of the target is unique, if $z_0$ were the true and correct z coordinate of the target then formulations (3) and (6) would yield identical values, or approximately equal, within an acceptable level of tolerance, $\varepsilon_x$.

$$|x_{(3)} - x_{(6)}| < \varepsilon_x \quad (7)$$

If (3) and (6) are outside an acceptable tolerance $\varepsilon_x$ then the iteration continues and a new estimate for z is tried, $z_1$. In accordance with some embodiments, the new estimate is defined automatically. For example, $z_1 = z_0 + \Delta$, where $\Delta$ is the size of the iteration step. In general, at $k^{th}$ iteration $z_k = z_{k-1} + \Delta$. The iterative process stops when condition (7) is met. A smaller $\Delta$ yields increased accuracy in determining the correct target coordinates, but would also require more computational time to complete the process, hence an increased latency. An increased latency may results in delays between surgical instrument movement and its visualization by the operating surgeon. In other words, the surgeon may perceive the system as lagging behind his commands. For a surgical viewing space of 20-30 cm of depth, a $\Delta$ of 0.1-0.3 mm may be sufficient. Of course, a person skilled in the art would know to balance the size of $\Delta$ against the computational required to complete the iterative process.

The above explanation has been simplified for presentation reasons and, therefore, it included only three sensors, $S_{11}$, $S_{12}$ and $S_{13}$. In general, more sensors can be used to increase the accuracy of Q3D coordinate computations but also to reduce the overall number of iterations. For example, if more than three sensors are used, preferably an array of 3×3 sensors, then methods such as the steepest gradient may be employed to trend the direction of estimation errors made by modules 402.5 and 403. The iterative step size and direction can then be adjusted to match the progression towards the local extreme of the 3D error gradient surface.

Guiding Endoscopic Surgery with Q3D Information

Figure 20:
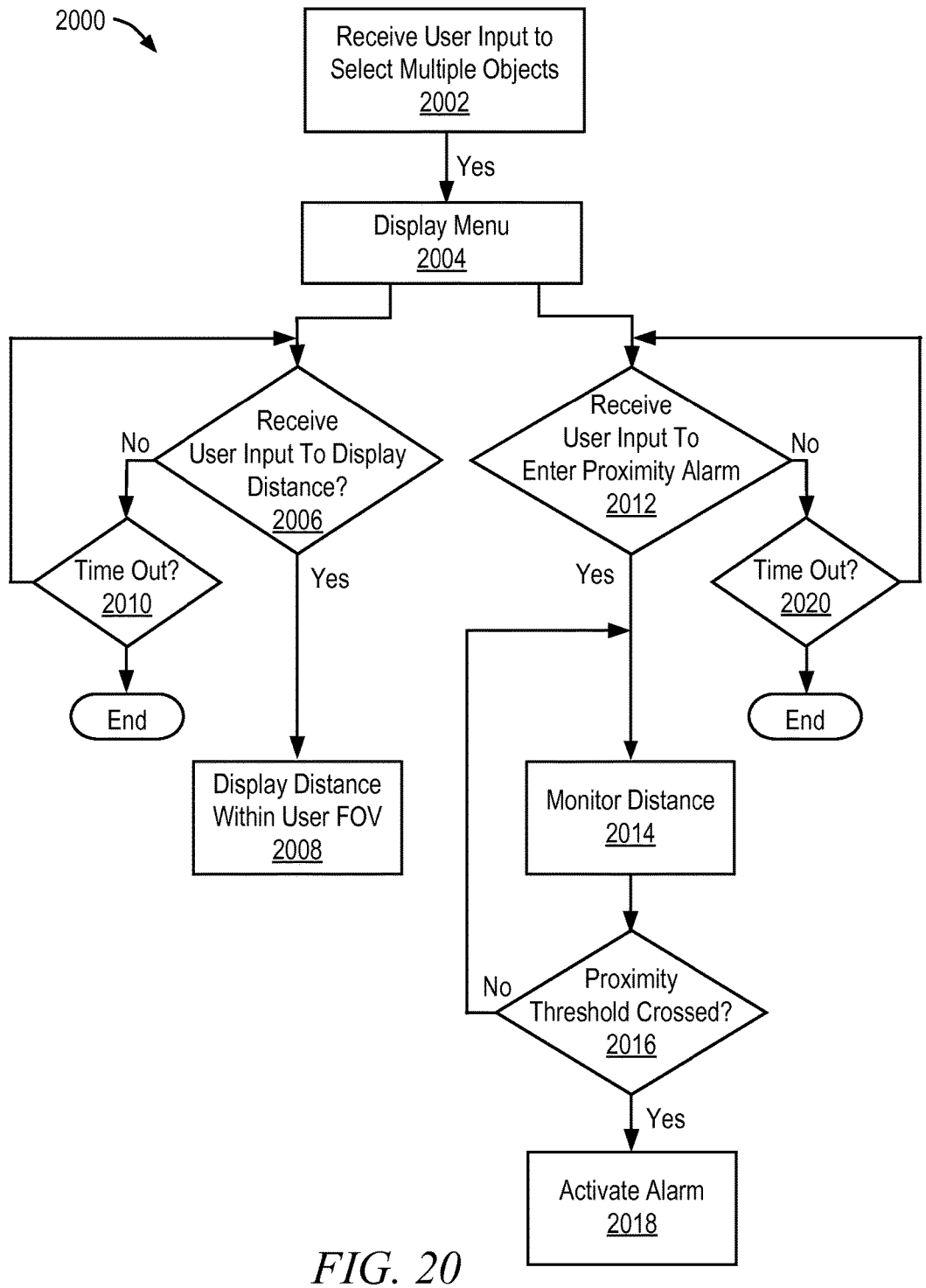
FIG. 20 is an illustrative flow diagram representing a first process to use Q3D information during a surgical procedure in accordance with some embodiments.

FIG. 20 is an illustrative flow diagram representing a first process 2000 to use Q3D information during a surgical procedure in accordance with some embodiments. Computer program code configures the computer 151 to perform the process 2000. Module 2002 configures the computer to receive user input to select at least two objects within a surgeon's field of view when looking in to the viewer 312. Module 2004 configures the computer to display a menu on a computer console in response to receipt of a user selection. Decision module 2006 configures the computer to determine whether user input to the menu is received to display a distance. In response to a determination that user input is received to display a distance, module 2008 configures the computer to display a numerical distance within the video image in the surgeon's field of view. Decision module 2010 configures the computer to wait for a prescribed time interval for receipt of user input to select distance display and to end operation of decision module 2006 in response to no receipt of user input within a 'time out' interval.

Decision module 2012 configures the computer to determine whether user input to the menu is received to enter a proximity alarm limit. In response to a determination that user input is received to enter a proximity threshold, module 2014 configures the computer to use Q3D information to monitor proximity between two or more objects within the surgeon's field of view. Decision module 2016 determines whether the proximity threshold has been crossed. In response to a determination that the proximity threshold has been crossed, module 2018 configures the computer to activate an alarm. The alarm may include a sound, a visual queue such as a blinking light or locking of instrument movement to avoid collision. In response to a determination that the proximity threshold has not been crossed, control flows back to monitoring module 2014. Decision module 2020 configures the computer to wait for the prescribed time interval for receipt of user input to enter the proximity threshold and to end operation of decision module 2012 in response to no receipt of user input within the 'time out' interval.

Figure 21:
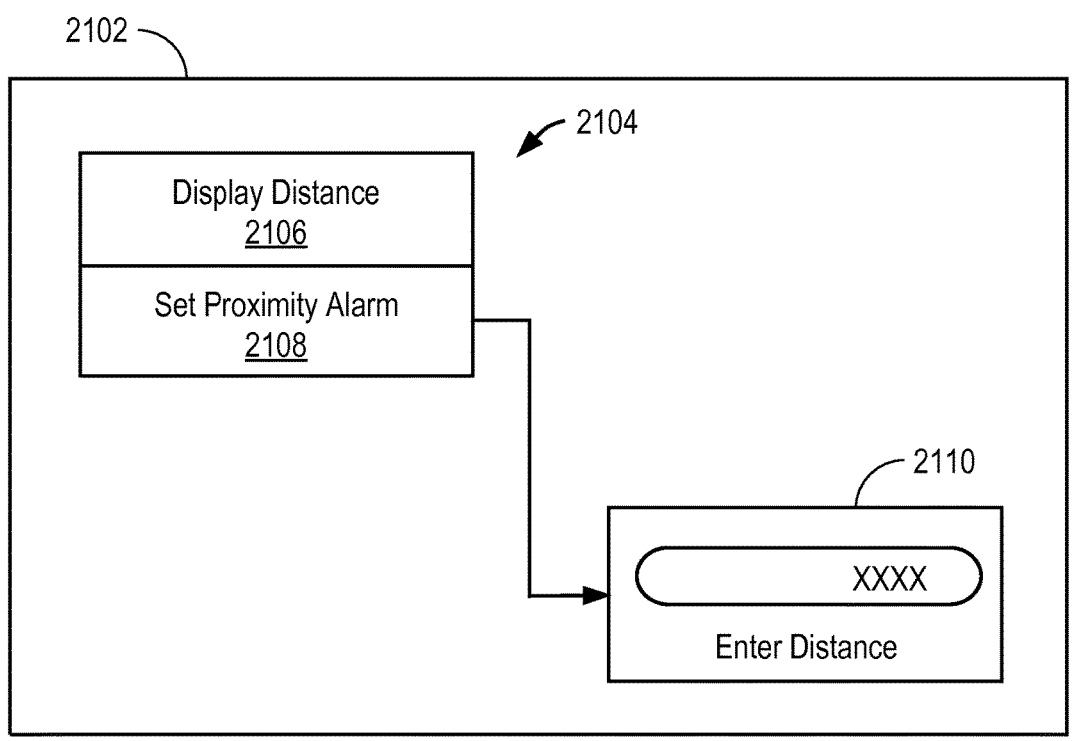
FIG. 21 is an illustrative drawing showing menu selections displayed on a display screen in accordance with the process of FIG. 20 in accordance with some embodiments.

FIG. 21 is an illustrative drawing showing menu selections displayed on a display screen 2102 in accordance with the process of FIG. 20 in accordance with some embodiments. The display screen 2102 includes a viewing monitor associated with the computer 151. Alternatively, the display screen 2102 may include a region of the imaging elements 206R, 206L of the viewer 312. In response to user input, module 2004 causes the display of a menu 2104 that includes a first menu item 'Display Distance' 2106 and a second menu item 'Set Proximity Alarm' 2108. In response to user input to select the 'Display Distance' menu item 2106, module 2008 causes a display of Q3D distance between two or more objects. Referring again to FIG. 4, there is shown a display of a Q3D distance "d_Instr_Trgt" between an instrument 400 and target displayed using module 2008. In response to user input to select the 'Set Proximity Alarm' menu item 2108, an 'Enter Distance' UI input 2110 is displayed that includes a field in which a user can enter a proximity distance threshold value, e.g., "xxxx millimeters". In an alternative embodiment (not shown), a default proximity threshold may be set in advance for all instruments, and a user may change the proximity threshold using the menu of FIG. 21, for example. In the alternative embodiment, a user can choose to elect the default threshold value rather than enter a threshold value. In some embodiments, a user can select both to display the distance and set a proximity alert.

Figure 22A:
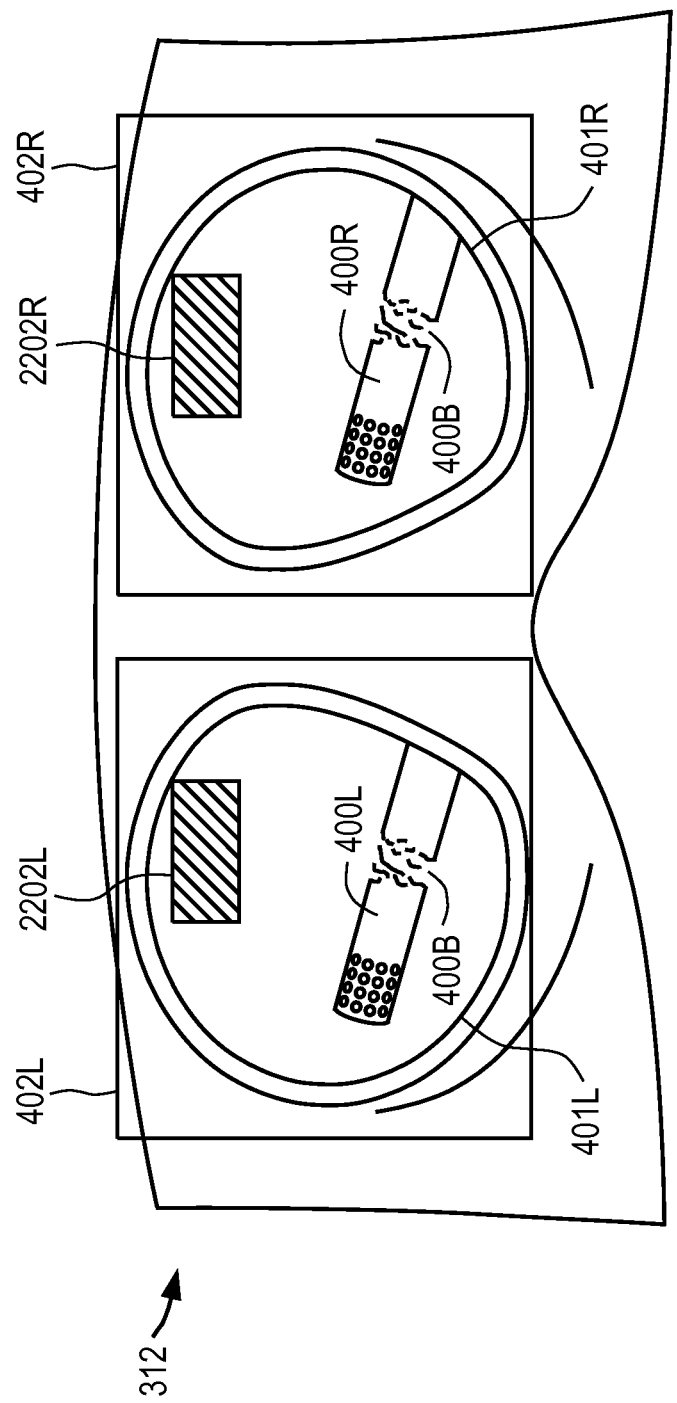
FIGS. 22A-22B are illustrative drawings representing certain details of receiving user input in accordance with the process of FIG. 20 in accordance with some embodiments.
Figure 22B:
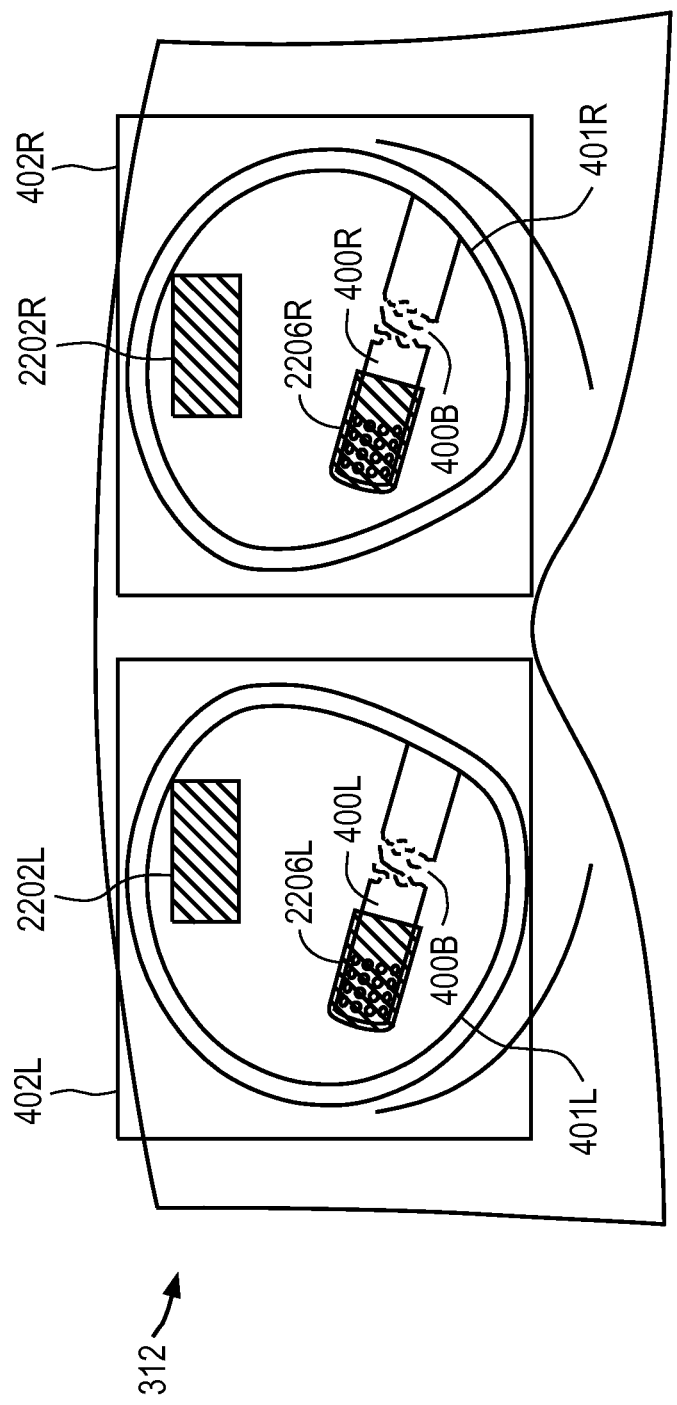

FIGS. 22A-22B are illustrative drawings representing certain details of receiving user input in accordance with the process of FIG. 20 in accordance with some embodiments. FIG. 22A shows example first highlighting 2202L, 2202R of a target 410L, 410R, such as body tissue, which can be created using video marker tool, such as telestration, or using the surgeon console manipulating control input devices 160 of FIG. 4. FIG. 22B shows example second highlighting 2206L, 2206R of an instrument tip 400L, 400R, which can be created using the video marker tool. In operation in accordance with some embodiments, a user creates the first highlighting 2202L, 2202R. Next, the user creates second highlighting 2206L, 2206R of the instrument tip 400L, 400R using video marker tool. It will be understood that the order in which items are highlighted is unimportant. The user then actuates a selector (not shown) (e.g., press the ENTER key) to enter the selection. Module 2002 interprets the received user input as selection of the target image 410L, 410R and the instrument image 400L, 400R.

Figure 23:
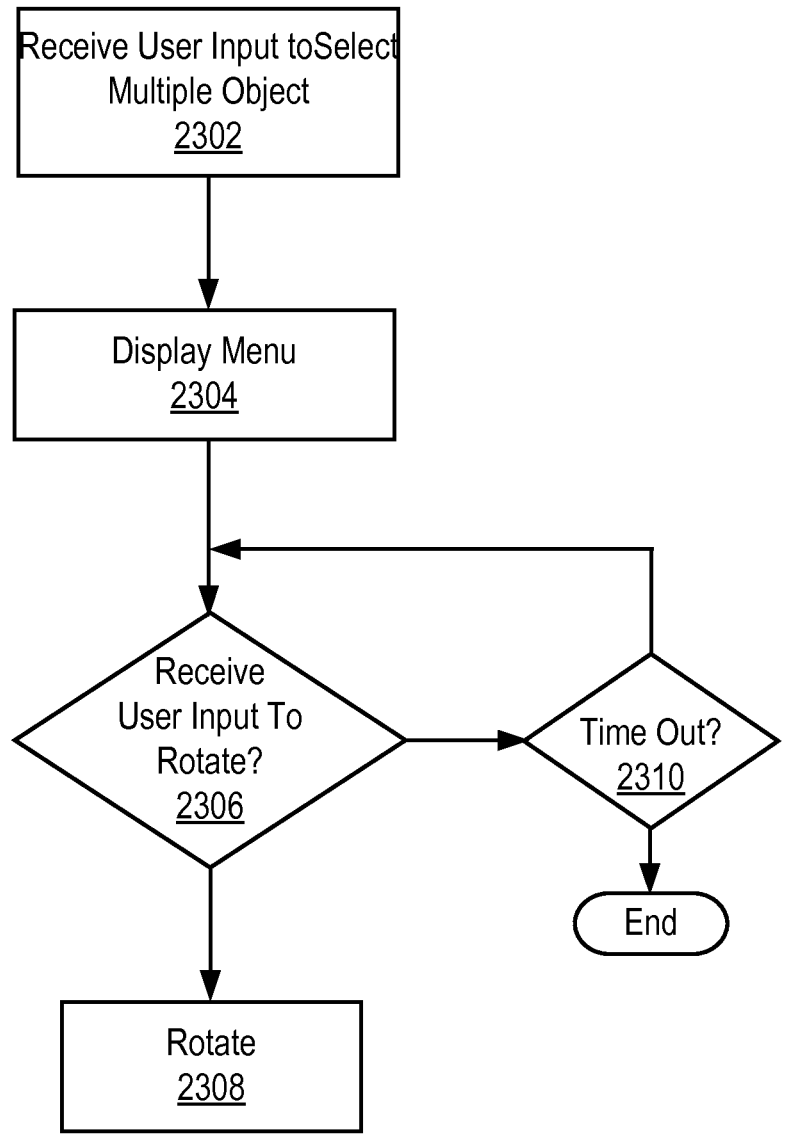
FIG. 23 is an illustrative flow diagram representing a second process to use Q3D information during a surgical procedure in accordance with some embodiments.

FIG. 23 is an illustrative flow diagram representing a second process 2300 to use Q3D information during a surgical procedure in accordance with some embodiments. Computer program code configures the computer 151 to perform the process 2300. Module 2302 configures the computer to receive user input to select an object within a surgeon's field of view when looking in to the viewer 312. For example, referring again to FIG. 22A, user input is shown received to create the second highlighting 2206L, 2206R of the instrument tip 400L, 400R using the video marker tool. User input (not shown) is received to actuate a selector (not shown) (e.g., press the ENTER key) to enter the selection of the image of the instrument tip 400L, 400R.

Returning once again to FIG. 23, in response to receipt of a user selection, module 2304 configures the computer to display a menu on a computer console. Decision module 2306 configures the computer to determine whether user input to the menu is received to rotate an image of a selected object. In response to a determination that user input is received to rotate an image, module 2308 configures the computer to display rotate the image to show a different three-dimensional perspective of the object. Decision module 2310 configures the computer to wait for a prescribed time interval for receipt of user input to rotate an image and to end operation of decision module 2306 in response to no receipt of user input within a 'time out' interval.

Figure 24:
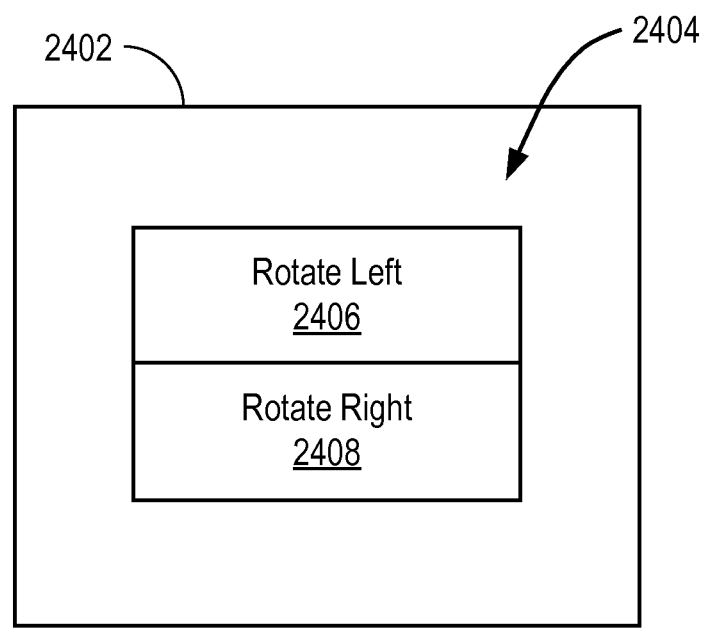
FIG. 24 is an illustrative drawing showing menu selections displayed on a display screen in accordance with the process of FIG. 23 in accordance with some embodiments.

FIG. 24 is an illustrative drawing showing menu selections displayed on a display screen 2402 in accordance with the process of FIG. 23 in accordance with some embodiments. The display screen 2402 includes a viewing monitor associated with the computer 151. Alternatively, the display screen 2402 may include a region of the imaging elements 206R, 206L of the viewer 312. In response to received user input, module 2304 causes the display of a menu 2404 that includes a third menu item 'Rotate Left' 2406 and a fourth menu item 'Rotate Right' 2408. In response to user input to select one or the other of the third or fourth menu items 2406, 2408, module 2308 uses the causes a rotation of the 3D model created and stored pursuant to module 407 of FIG. 9. It will be appreciated that the amount of rotation may be limited to a few degrees, less than 30 degrees for example, since the sensor imager array 210 has a limited overall field of view.

The foregoing description and drawings of embodiments in accordance with the present invention are merely illustrative of the principles of the invention. Therefore, it will be understood that various modifications can be made to the embodiments by those skilled in the art without departing from the spirit and scope of the invention, which is defined in the appended claims.

The invention claimed is:

1. A device comprising:
   an endoscope; an image sensor array comprising at least three imaging sensors having coplanar overlapping fields of view, disposed to image fields of view adjacent to the endoscope, wherein each imaging endoscope,
   wherein each imaging sensor including a pixel array that is separate from the pixel arrays of other imaging sensors; and a light source disposed to illuminate the field of view; wherein the endoscope includes an elongated portion having a first end portion and a second end portion opposite the first end portion; wherein the image sensor array is disposed displaced from the first end portion of the endoscope, closer to the second end portion of the endoscope; the device further including; a light pipe disposed to transmit an image from a field of view adjacent the first end portion of the endoscope to the image sensor array displaced from the first end portion, closer to the second end portion of the endoscope.

2. The device of claim 1,
   wherein the light source produces only non-structured light.

3. The device of claim 1,
   wherein the light source produces white light.

4. The device of claim 1,
   wherein the light source produces white light.

5. The device of claim 1,
   wherein an end of the endoscope opposite the first end portion of the elongated portion is configured for mechanical coupling with a mechanical surgical arm.

6. A device comprising:
   an endoscope; an image sensor array disposed to image a field of view adjacent to the endoscope, each sensor including a pixel array that is separate from the pixel arrays of other sensors;
   and a light source disposed to illuminate the field of view:
   and a controller configured to: determine a three-dimensional location of a target object based upon image information captured by the image sensor array; wherein the controller is configured to identify pixels in each of multiple image sensors that are wherein identifying pixels includes using a correlation process to match image projections of the same target object in each of multiple image sensors;

wherein determining the three-dimensional location includes determining an estimated location of the target object in at least one dimension based at least in part upon relative positions of at least three identified pixels;

and in response to the determined estimated location differing by more than an acceptable tolerance, repeating the correlation process to refine the matching of image projections.

7. The device of claim 6, wherein the three-dimensional location of the target object is determined based at least in part upon a pixel-distance relationship between identified pixels and the physical characteristics of the image sensor array.

8. The device of claim 6, wherein the controller is configured to identify pixels in each of multiple image sensors of the image sensor array that are illuminated by projections from the same target object.

9. The device of claim 8, wherein identifying pixels includes matching image projections of a same target object in each of multiple arrays of the image sensor array.

10. A device comprising:

an endoscope; an image sensor array disposed to image a field of view adjacent to the endoscope, each sensor including a pixel array that is separate from the pixel arrays of other sensors;

and a light source disposed to illuminate the field of view; and a controller configured to, determine a three-dimensional location of a target object based upon image information captured by the image sensor array;

wherein the controller is configured to identify pixels in each of multiple image sensors that are illuminated by projections from the same target object; and wherein identifying pixels includes using a correlation process to match image projections of the same target object in each of multiple image sensors wherein determining the three-dimensional location includes determining an estimated location of the target object in at least one physical dimension generally parallel to a plane of the sensors based upon relative positions of at least three identified pixels;

and in response to the determined estimated location matching to within an acceptable tolerance, determining an estimated physical location of the target object in at least one other physical dimension generally perpendicular to the plane of the sensors based at least in part upon the determined physical location of the target object in the at least one physical dimension.

* * * * *